US012799465B2

(12) United States Patent
Gil-Henn et al.

(10) Patent No.: US 12,799,465 B2
(45) Date of Patent: Nov. 17, 2026

(54) Pyk2-DERIVED PEPTIDES FOR INHIBITING INVADOPODIA-MEDIATED CANCER METASTASIS

(71) Applicant: BAR-ILAN UNIVERSITY, Ramat Gan (IL)

(72) Inventors: Hava Gil-Henn, Karmiel (IL); Jordan Chill, Kiryat Ono (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 249 days.

(21) Appl. No.: 18/648,360

(22) Filed: Apr. 27, 2024

(65) Prior Publication Data

US 2024/0368566 A1 Nov. 7, 2024

Related U.S. Application Data

(60) Provisional application No. 63/499,265, filed on May 1, 2023.

(51) Int. Cl.
*C12N 9/12* (2006.01)
*A61P 35/04* (2006.01)
*A61K 38/00* (2006.01)

(52) U.S. Cl.
CPC ................ *C12N 9/12* (2013.01); *A61P 35/04* (2018.01); *C12Y 207/10002* (2013.01); *A61K 38/00* (2013.01); *C07K 2319/10* (2013.01); *C07K 2319/72* (2013.01)

(58) Field of Classification Search
CPC ........................................................ C12N 9/12
See application file for complete search history.

(56) References Cited

PUBLICATIONS

Twafra (A novel Pyk2-derived peptide inhibits invadopodia-mediated breast cancer metastasis. Oncogene 42, 278-292 (2023). Published on-line on Oct. 18, 2022 (Year: 2022).*

Fransceus. J Ind Microbiol Biotechnol. May 2017;44(4-5):687-695 (Year: 2017).*

Sanavia. Computational and Structural Biotechnology Journal, vol. 18, 2020, pp. 1968-1979. (Year: 2020).*

Studer. Residue mutations and their impact on protein structure and function: detecting beneficial and pathogenic changes. Biochem. J. (2013) 449, 581-594. (Year: 2013).*

Saksela K, Permi P. SH3 domain ligand binding: What's the consensus and where's the specificity? FEBS Lett 2012; 586: 2609-2614. doi: 10.1016/j.febslet.2012.04.042.

Schlaepfer DD, Mitra SK. Multiple connections link FAK to cell motility and invasion. Curr Opin Genet Dev 2004; 14: 92-101. doi: 10.1016/j.gde.2003.12.002. PMID: 15108811.

Lev S, Moreno H, Martinez R, Canoll P, Peles E, Musacchio JM et al. Protein tyrosine kinase PYK2 involved in Ca(2+)-induced regulation of ion channel and MAP kinase functions. Nature 1995; 376: 737-745. doi: 10.1038/376737a0. PMID: 7544443.

Lipinski CA, Loftus JC. Targeting Pyk2 for therapeutic intervention. Expert Opin Ther Targets 2010; 14: 95-108. doi: 10.1517/14728220903473194. PMID: 20001213; PMCID: PMC2943731.

Tomar A, Lawson C, Ghassemian M, Schlaepfer DD. Cortactin as a target for FAK in the regulation of focal adhesion dynamics. PLoS One 2012; 7: e44041. doi: 10.1371/journal.pone.0044041.

Genna A, Lapetina S, Lukic N, Twafra S, Meirson T, Sharma VP et al. Pyk2 and FAK differentially regulate invadopodia formation and function in breast cancer cells. J Cell Biol 2018; 217: 375-395. doi: 10.1083/jcb.201702184.

Eckert MA, Lwin TM, Chang AT, Kim J, Danis E, Ohno-Machado L et al. Twist1-induced invadopodia formation promotes tumor metastasis. Cancer Cell 2011; 19: 372-386. doi: 10.1016/j.ccr.2011.01.036. PMID: 21397860; PMCID: PMC3072410.

Hashimoto S, Hirose M, Hashimoto A, Morishige M, Yamada A, Hosaka H et al. Targeting AMAP1 and cortactin binding bearing an atypical src homology 3/proline interface for prevention of breast cancer invasion and metastasis. Proc Natl Acad Sci U S A 2006; 103: 7036-7041. doi: 10.1073/pnas.0509166103.

Kim J, Lee CD, Rath A, Davidson AR. Recognition of non-canonical peptides by the yeast Fus1p SH3 domain: elucidation of a common mechanism for diverse SH3 domain specificities. J Mol Biol 2008; 377: 889-901. doi: 10.1016/j.jmb.2008.01.063.

Feng S, Kasahara C, Rickles RJ, Schreiber SL. Specific interactions outside the proline-rich core of two classes of Src homology 3 ligands. Proc Natl Acad Sci U S A 1995; 92: 12408-12415. doi: 10.1073/pnas.92.26.12408. PMID: 8618911; PMCID: PMC40367.

Hayes KE, Walk EL, Ammer AG, Kelley LC, Martin KH, Weed SA. Ableson kinases negatively regulate invadopodia function and invasion in head and neck squamous cell carcinoma by inhibiting an HB-EGF autocrine loop. Oncogene 2013; 32: 4766-4777. doi: 10.1038/onc.2012.513.

Hashimoto A, Hashimoto S, Ando R, Noda K, Ogawa E, Kotani H et al. GEP100-Arf6-AMAP1-cortactin pathway frequently used in cancer invasion is activated by VEGFR2 to promote angiogenesis. PLoS One 2011; 6: e23359. doi: 10.1371/journal.pone.0023359.

(Continued)

*Primary Examiner* — Yong D Pak

(74) *Attorney, Agent, or Firm* — The Roy Gross Law Firm, LLC; Roy D. Gross

(57) ABSTRACT

The present invention relates to an isolated Pyk2-derived peptide comprising a consensus proline-rich region 2 (PRR2) sequence, wherein the consensus PRR2 sequence is PxxPx(R/K)P(K/R)(Y/W/F) in which "x" stands for any amino acid; and the peptide is capable of inhibiting metastasis by binding to a Src homology 3 (SH3) domain of cortactin. The present invention further provides methods of treating cancer and for preventing or inhibiting cancer invasion and/or metastasis by administering the isolated Pyk2-derived peptide of the invention, optionally in combination with an anti-cancer agent.

18 Claims, 22 Drawing Sheets
(12 of 22 Drawing Sheet(s) Filed in Color)
Specification includes a Sequence Listing.

(56) References Cited

PUBLICATIONS

Meirson T, Genna A, Lukic N, Makhnii T, Alter J, Sharma VP et al. Targeting invadopodia-mediated breast cancer metastasis by using ABL kinase inhibitors. Oncotarget 2018; 9: 22158-22183. doi: 10.18632/oncotarget.25243. PMID: 29774130; PMCID: PMC5955141.

Gil-Henn H, Patsialou A, Wang Y, Warren MS, Condeelis JS, Koleske AJ. Arg/Abl2 promotes invasion and attenuates proliferation of breast cancer in vivo. Oncogene. May 23, 2013;32(21):2622-30. doi: 10.1038/onc.2012.284. Epub Jul. 9, 2012. PMID: 22777352; PMCID: PMC3473103.

* cited by examiner

Pyk2-DERIVED PEPTIDES FOR INHIBITING INVADOPODIA-MEDIATED CANCER METASTASIS

CROSS REFERENCE TO RELATED APPLICATIONS

This application claims the benefit of U.S. Provisional Application No. 63/499,265 filed on May 1, 2023. Any and all applications for which a foreign or domestic priority claim is identified above and/or in the Application Data Sheet as filed with the present application are hereby incorporated by reference under 37 CFR 1.57.

FIELD OF THE INVENTION

The present invention is generally directed to treatment of cancer. More specifically, the invention relates to treatment of cancer by inhibiting cancer metastasis.

BACKGROUND OF THE INVENTION

Metastatic dissemination of cancer cells from the primary tumor and their spread to distant tissues and organs is the leading cause of mortality in breast cancer patients. Although cytotoxic drugs and hormone-blocking therapeutics are often used to shrink the primary tumor or prevent disease recurrence, no treatment to permanently eradicate metastatic breast cancer exists at present.

Metastatic cancer cells leaving the primary tumor use invasive feet-like structures called invadopodia, actin-rich protrusions with extracellular matrix (ECM) degrading activity, to invade through the basement membrane and to intravasate into blood vessels and spread to distant tissues and organs throughout the body. Invadopodia were identified in several invasive cancer cell lines, such as breast, head and neck, prostate, fibrosarcoma, and melanoma as well as in primary tumor cells. Moreover, direct molecular links between invadopodia assembly and cancer metastasis have previously been demonstrated in both mice models and human patients. Along these lines, the inventors have recently shown that therapeutic inhibition of invadopodia formation and function can block breast cancer metastasis in a xenograft mouse model.

The actin-nucleation promoting factor cortactin is a crucial regulator of actin cytoskeleton remodeling and an essential component of invadopodia. Cortactin plays an imperative role in actin polymerization-mediated membrane protrusions, cell migration, cell-cell adhesion, endocytosis, and neuronal synapse stabilization. Its five functional regions include an N-terminal acidic domain (NTA) that binds the Arp3 component of the Arp2/3 complex and synergizes with the N-WASP VCA domain to promote actin polymerization, six and a half F-actin-binding repeats of 37 amino acids each, an α-helical domain with unknown function, a proline-serine-threonine (PST) rich phosphorylation region enabling cortactin to integrate signals from diverse upstream signaling cascades, and a Src homology 3 (SH3) domain (residues 495-550). The SH3 domain mediates the association of cortactin with various signaling proteins such as dynamin, Wiskott-Aldrich Syndrome (WASp)-interacting protein (WIP), CortBP-1/Shank2, Shank-3, ZO-1, and faciogenital dysplasia protein (Fgd1). The association of cortactin with proline-rich regions of diverse proteins enables regulating diverse actin remodeling-mediated cellular processes, such as endocytosis, lamellipodial protrusions, and cell migration. Amplification of the CTTN gene (encoding cortactin) followed by overexpression of cortactin have been observed in various human cancers and are associated with poor patient prognosis. Importantly, cortactin is an essential component of invadopodia, regulating both their assembly and the trafficking and secretion of matrix metalloproteinases (MMPs) from invadopodia tips. Cortactin phosphorylation on tyrosine residues regulates an on-off switch which initiates actin polymerization in invadopodia, leading to their maturation and activation and consequent tumor cell invasion.

Complexes between SH3 domains and proline-rich polypeptide segments are well-known regulators of major intracellular signaling events. A key feature is the steric compatibility between a flat SH3 hydrophobic surface with three grooves delineated by conserved aromatic residues and a PxxP core adopting a left-handed helical conformation known as the polyproline II helix, recently also termed κ-helix. Typically, two qP dipeptides (q being a hydrophobic residue) fill binding pockets between the conserved aromatic residues, and the inherent symmetry of the PxxP helix allows for binding in both possible orientations. The location of flanking basic residues and their interaction with negatively charged residues in the SH3 specificity pocket determines the preferred binding pose, roughly dividing SH3 ligands into class I and class II motifs, exhibiting N-terminal or C-terminal basic residues, respectively. Screening of a phage-displayed peptide library defined the cortactin-binding consensus motif as +PPΨPxKP (SEQ ID NO: 25) ('Ψ' is an aliphatic residue, >90% conserved positions in bold), a class II motif with an additional PxxP motif, sometimes termed a class VIII motif. However, structure determination of SH3/PxxP complexes is highly challenging due to their moderate affinity levels, which are in the micromolar range. Limited information at atomic resolution restricts a deeper structural understanding of cortactin SH3-PRR regulatory complexes.

Proline-rich tyrosine kinase 2 (Pyk2), along with focal adhesion kinase (FAK), include a subfamily of non-receptor protein tyrosine kinases that integrate signals from various receptors, activating signaling pathways that regulate proliferation, migration, and invasion in numerous cell types. Both share a conserved domain structure, consisting of an N-terminal FERM domain, a central catalytic kinase domain, three proline-rich sequences, and a C-terminal FAT domain. Two of the proline-rich sequences, proline-rich region 2 ($^{713}$Pro-Pro-Pro-Lys-Pro-Ser-Arg-Pro$^{720}$ of UniProt Acc. No. Q14289) (PRR2, SEQ ID NO: 26) and proline-rich region 3 ($^{855}$Pro-Pro-Gln-Lys-Pro-Pro-Arg-Leu$^{862}$) (PRR3, SEQ ID NO: 27) are major sites for SH3-mediated protein-protein interactions. The former exhibits high similarity between the two kinases, while the latter shows very little similarity, possibly accounting for their unique binding partners. Interestingly, a previous study showed that cortactin SH3 binds directly to both FAK-PRR2 and FAK-PRR3, an interaction followed by a sequence of events that promote focal adhesion turnover and cell migration.

Accordingly, the progress in understanding the interactions between cortactin and tyrosine kinases may be harnessed for the development of the much needed therapeutics for inhibiting cancer metastases.

SUMMARY OF INVENTION

The following embodiments and aspects thereof are described and illustrated in conjunction with compositions and methods which are meant to be exemplary and illustrative, not limiting in scope. In various embodiments, one or more of the above-described problems have been reduced or eliminated, while other embodiments are directed to other advantages or improvements.

The inventors designed a cell-permeable peptide inhibitor that contains the second proline-rich region (PRR2) sequence of Pyk2, which binds to the SH3 domain of cortactin and blocks spontaneous lung metastasis in immune-competent mice by inhibiting invadopodia maturation and function In some embodiments, the present invention provides an isolated Pyk2-derived peptide including a consensus proline-rich region 2 (PRR2) sequence, wherein the consensus PRR2 sequence is PxxPx(R/K)P(K/R)(Y/W/F) in which "x" stands for any amino acid; and the peptide is capable of inhibiting metastasis by binding to a Src homology 3 (SH3) domain of cortactin.

In some embodiments, the peptide includes a sequence at least 70%, 75%, 80%, 85%, 90%, 95%, or 99% identical to a sequence including the second proline-rich region of Pyk2.

In some embodiments, the peptide has a length of about 9-100, 9-50, 10-30, or 15-25 amino acids.

In some embodiments, the consensus PRR2 sequence is PxxPxRPKY (SEQ ID NO: 12). In some embodiments, the consensus PRR2 sequence is PPKPSRPKY (SEQ ID NO: 24).

In some embodiments, the peptide includes a sequence at least 70%, 75%, 80%, 85%, 90%, 95%, or 99% identical to the sequence set forth in SEQ ID NO: 1.

In some embodiments, the peptide does not include a complete Pyk2 sequence. In some embodiments, the peptide does not include a proline-rich region 3 (PRR3) sequence of a Pyk2 protein.

In some embodiments, the peptide includes at least one proline outside the consensus PRR2 sequence. In some embodiments, the peptide further includes a least one tag sequence selected from the group consisting of HIV-TAT, HAIYPRH, and combinations thereof. In some embodiments, the peptide includes at least one non-conventional amino acid and/or at least one modified amino acid. In some embodiments, the at least one non-conventional amino acid and/or modified amino acid is outside the consensus PRR2 sequence. In some embodiments, the peptide is a cyclic peptide. In some embodiments, the peptide is capped at the N-terminus, at the C-terminus, or at both the N- and the C-terminus.

In some embodiments, the peptide is not capable of inhibiting primary tumor growth. In some embodiments, the peptide does not inhibit primary tumor growth.

In some embodiments, the present invention provides a method of treating a cancer in a subject, the method including administering to the subject a therapeutically-effective dose of the isolated Pyk2-derived peptide disclosed herein.

In some embodiments, the treating includes inhibiting or preventing cancer invasion and/or cancer metastasis in the subject.

In some embodiments, the present invention provides a method of inhibiting or preventing cancer invasion and/or cancer metastasis in a subject, the method including administering to the subject a therapeutically-effective dose of the isolated Pyk2-derived peptide disclosed herein.

In some embodiments, the method further includes administering to the subject an anti-cancer treatment. In some embodiments, the anti-cancer treatment includes a chemotherapeutic agent and/or an immunotherapeutic agent.

In some embodiments, the cancer includes invadopodia.

In some embodiments, the cancer is invasive or metastatic.

In some embodiments, the cancer is not invasive or is not metastatic.

In some embodiments, the cancer is selected from the group consisting of breast cancer, pancreatic cancer, head and neck cancer, prostate cancer, fibrosarcoma, and melanoma.

In some embodiments, the administration is intravenous, intramuscular, subcutaneous, intratumoral, or intraperitoneal.

In addition to the exemplary aspects and embodiments described above, further aspects and embodiments will become apparent by reference to the figures and by study of the following detailed descriptions.

BRIEF DESCRIPTION OF DRAWINGS

The patent or application file contains at least one drawing executed in color. Copies of this patent or patent application publication with color drawings will be provided by the Office upon request and payment of necessary fee.

The invention will now be described in relation to certain examples and embodiments with reference to the following illustrative figures.

FIG. 1A. mRNA expression analysis of 1,905 samples originating from TCGA with different hormone receptor statuses. Left to right each set: ER, estrogen receptor positive; PR, progesterone receptor positive; HER2, HER2 positive; TN, triple negative. FIG. 1B. Comparison of protein abundance in 102 samples from different hormone receptor statuses. Data titles are the same as in FIG. 1A. FIG. 1C. mRNA expression levels of PTK2B and CTTN in metastatic (right each pair) versus non-metastatic (left each pair) breast cancer patients is shown in boxplots. Metastasis was defined as occurrence of distant metastasis event within the follow-up period. The boxes in FIGS. 1A, 1B and 1C are delimited by the lower and upper quartile, the horizontal red line indicates the sample median, the notches represent the 95% confidence interval (CI), and whiskers extend to the most extreme point which is no more than 1.5 times the interquartile range from the box. Outliers are shown as points beyond boxplot whiskers. P values were calculated using two-tailed Student's t-test. FIGS. 1D-1F. Kaplan-Meier curves of DMFS in 1,650 breast cancer cases. Microarray data (Affymatrix) were obtained from the NCBI Gene Expression Omnibus (GEO) data repository. Tumor samples were split into high (blue) and low (red) expression groups based on mRNA gene expression with z-score cut-off value 0. Shown are DMFS survival curves for PTK2B, HR: 1.06 [95% CI: 0.86-1.30] ρ=6.2e-01 (FIG. 1D), CTTN, HR: 1.58 [95% CI: 1.29-1.93] ρ=1.0e-05 (FIG. 1E), and their combination HR: 1.72 [95% CI: 1.29-2.30] ρ=3.5e-04, SI: 1.13 (FIG. 1F). P values were calculated by log-rank test, hazard ratio (HR) and 95% confidence interval (CI) are shown. Synergy index (SI) is indicated for evaluation of PTK2B+CTTN in (FIG. 1F).

FIG. 2A. Representative images of metastatic 4T1 resistant colonies from control (scrambled), Pyk2-PRR2, and Pyk2-PRR3 treated mice. FIG. 2B. Metastatic colonies: quantification of colonies from 1:10 dilution of dissociated lung cells. Each colony originated from one metastatic cell. n=7 (scrambled), n=7 (Pyk2-PRR2), n=8 (Pyk2-PRR3) mice per group.  $P<0.01$ by one-way ANOVA with Tukey's post-hoc test. Error bars represent SEM. FIGS. 2C-2D. Primary tumors were dissected at the end of the experiment (24 h following the last peptide injection), and tumor volume and weight were measured. n=9 (scrambled), n=9 (Pyk2-PRR2), n=10 (Pyk2-PRR3) tumors per group. Scale bar, 1 cm. FIG. 2E. Proliferation: quantification of PCNA positive cells normalized to DAPI positive cells. The average percentage of proliferating cells in total cells per field is shown. FIG. 2F. Apoptosis: quantification of apoptotic cells (cleaved caspase 3 positive cells). Shown is the number of apoptotic cells per field. FIG. 2**G. Angiogenesis: luantification of CD-31 positive blood vessels. For all quantifications, n=50 random fields from five tumors per condition.

FIG. 3A. Representative images from 3D scratch-wound assay movies of MDA-MB-231 cells treated with Pyk2-PRR or scrambled peptides at time 0 (upper panels) and 12 h (lower panels). Scale bar, 300 μm. FIGS. 3B, 3D, and 3F. Quantification of 3D directed motility towards a wound in Matrigel containing embedded MDA-MB-231 cells treated with Pyk2-PRR2 (red squares), Pyk2-PRR3 (blue triangles), or scrambled control (black circles) peptides. FIGS. 3C, 3E, and 3G. same as above, but normalized to MMP inhibitor-treated values. FIGS. 3B-3C: 0.1 μM; FIGS. 3D-3E: 1 μM; FIGS. 3F-G: 5 μM; n=3 independent experiments, each experiment was performed in triplicates. *$P<0.05$ (between scrambled and PRR2 and scrambled and PRR3 in FIG. 3B and in FIG. 3D, $P<0.01$ (between scrambled and PRR2 in FIG. 3**F., as determined by two-way ANOVA followed by Bonferroni post-hoc test. Error bars represent SEM.

FIG. 4A. NMR determination of SH3 binding of Pyk2 peptides PRR2 and PRR3. Details from the SH3 $^{1}H$,$^{15}N$-HSQC spectra acquired along a titration isotherm with focus on cortactin residues W525 (indole sidechain) and I521, A539 (backbone amide). Spectra were acquired at 0:1 (black), 0.5:1, 1:1, 2:1 and 4:1 (light green) mol:mol PRR2:SH3 and 0:1 (black), 0.75:1, 1.5:1, 3:1 and 6:1 (light green) mol:mol PRR3:SH3. In the W525 panel, the asterisk indicates a different (W526 indole) unaffected cross-peak. FIG. 4B. Binding isotherms showing the fraction of bound SH3 as a function of the PRR:SH3 mol:mol ratio, and the fitted curve providing the dissociation constant. Not shown is scrambled PRR2, for which a 6:1 peptide:SH3 mol:mol ratio exhibited a small effect on peak position, projecting to a low ($K_D$>1 mM) affinity for this peptide. FIG. 4C. Quantification of FRET between Pyk2-pY402 and cortactin in mature, matrix-degrading invadopodia of MDA-MB-231 cells treated with different peptide concentrations. n=42-66 invadopodia per group from three different experiments. FIG. 4D. Quantification of invadopodium precursors defined by co-localization of cortactin and Tks5. MDA-MB-231 cells were plated on Alexa 405-labeled gelatin and incubated with different concentrations of Pyk2-PRR or control scrambled peptides for 4 h, fixed, and labeled for cortactin and Tks5. n=136-153 (scrambled), n=143-155 (Pyk2-PRR2), n=156-160 (Pyk2-PRR3) cells from three different experiments. FIG. 4E. Quantification of mature (active) invadopodia, defined by co-localization of cortactin and Tks5 with degradation regions. n=138-153 (scrambled), n=143-155 (Pyk2-PRR2), n=156-160 (Pyk2-PRR3) cells from three different experiments. FIG. 4F. Quantification of matrix degradation by peptide-treated cells. MDA-MB-231 cells were plated on Alexa Fluor 568 FN/gelatin matrix in the presence of Pyk2-PRR or control peptides and allowed to degrade for 24 h. n=91-127 (scrambled), n=91-123 (Pyk2-PRR2), n=92-105 (Pyk2-PRR3) fields per group from three independent experiments. *$P<0.05$, $P<0.01$, *$P<0.001$, as determined by one-way ANOVA followed by Tukey's post-hoc test. Error bars represent SEM.

FIG. 5A. Quantification of pY-421-cortactin/cortactin-TagRFP signal at cortactin-rich puncta. MDA-MB-231 cells stably expressing cortactin-TagRFP (upper panels) were treated with Pyk2-PRR or control scrambled peptides, plated on FN/gelatin matrix, starved, and stimulated with EGF. Cells were then fixed and labeled for phosphorylated cortactin (anti-pY421-cortactin;) before (0 min, left bars) or after (3 min, right bars) EGF stimulation. n=42-129 (scrambled −EGF), n=43-131 (scrambled +EGF), n=42-142 (Pyk2-PRR2 −EGF), n=42-116 (Pyk2-PRR2 +EGF), n=41-92 (Pyk2-PRR3 −EGF), n=41-100 (Pyk2-PRR3 +EGF) puncta per group from three independent experiments. FIG. 5B. Quantification of free actin barbed ends as measured by the average biotin-actin intensity at stimulated invadopodia containing Arp2. MDA-MB-231 cells were treated with Pyk2-PRR or control scrambled peptides, plated on FN/gelatin matrix, starved, and left untreated (0 min EGF, left bars) or stimulated with EGF for three min (3 min EGF, right bars). Cells were fixed and labeled for Arp2 (left panels) as invadopodia marker and biotin-actin as a marker for newly formed barbed ends. n=107-246 invadopodia per group from three different experiments. *$P<0.05$,  $P<0.01$, *$P<0.001$, as determined by two-way ANOVA followed by Bonferroni post-hoc test. Error bars represent SEM.

FIG. 6A. Ribbon-representation of the complex showing the SH3 domain (grey, residue numbers in underlined grey) and the PRR2 peptide (cyan, residue numbers in black and italics). FIG. 6B. A view of the complex showing the interaction of PRR2 (cyan ribbon) with the SH3 surface. SH3 residues are colored according to their PRR2-induced chemical shift perturbation (CSP); the third, second, and top deciles (each spanning five residues) are colored in cyan, blue, and purple, respectively. Asterisks denote changes in the side-chain cross-peaks of Trp and Asn residues. FIG. 6C. Summary of PRR2-induced CSPs along the SH3 sequence, color-coding as in panel A, values for W525 and N540 are for side-chain CSPs. FIG. 6D. PRR2-induced CSPs for the Y722A mutant (light grey bars) and the A720-726 truncated peptide (dark grey bars). Changes are far more pronounced for the truncation mutant, supporting the importance and interactions of surface II.

FIG. 7A. Quantification of FRET between Pyk2-pY402 and cortactin in mature, matrix-degrading invadopodia of MDA-MB-231 cells stably expressing cortactin-TagRFP-WT and treated with either scrambled peptide, Pyk2-PRR2, or Pyk2 super-mutant peptides at different peptide concentrations. n=68-72 invadopodia per group from three different experiments. FIG. 7B. Quantification of invadopodium precursors defined by co-localization of cortactin and Tks5.MDA-MB-231 cells were plated on Alexa 405-labeled gelatin and incubated with different concentrations of control, Pyk2-PRR2, or Pyk2 super-mutant for 4 h, fixed, and labeled for cortactin (red) and Tks5 (green). Boxed regions and insets depict co-localization of cortactin and Tks5 as markers of invadopodium precursors and Alexa 405 gelatin as a marker of mature invadopodia. n=158-178 (scrambled), n=141-154 (Pyk2-PRR2), n=141-174 (Pyk2 super-mutant) cells from three independent experiments. FIG. 7C. Quantification of mature (active) invadopodia, defined by co-localization of cortactin and Tks5 with degradation regions. n=158-178 (scrambled), n=141-154 (Pyk2-PRR2), n=141-174 (Pyk2 super-mutant) cells from three independent experiments. FIG. 7D. Quantification of matrix degradation by peptide-treated cells. MDA-MB-231 cells were plated on Alexa Fluor 568 FN/gelatin matrix in the presence of control scrambled, Pyk2-PRR2, or Pyk2 super-mutant and allowed to degrade for 24 h. n=115 (scrambled), n=106 (Pyk2-PRR2), n=120 (Pyk2 super-mutant) cells from three independent experiments. P<0.01, *P<0.001, as determined by one-way ANOVA followed by Tukey's post-hoc test. Error bars represent SEM.

FIG. 8A-8B. Primary tumors were dissected at the end of the experiment (24 h following the last peptide injection), and tumor volume and weight were measured. n=8 (scrambled), n=8 (Pyk2-PRR2), n=7 (Pyk2 super-mutant) tumors per group. FIG. 8C. Proliferation: quantification of PCNA positive cells normalized to DAPI positive cells. The average percentage of proliferating cells in total cells per field is shown. FIG. 8D. Apoptosis: quantification of apoptotic cells (cleaved caspase 3 positive cells). Shown is the number of apoptotic cells per field. FIG. 8E. Angiogenesis: quantification of CD-31 positive blood vessels. n=44 (scrambled), n=47 (Pyk2-PRR2), n=47 (Pyk2 super-mutant) random fields from 5 tumors per condition. FIG. 8F. Representative images of metastatic 4T1 resistant colonies from control, Pyk2-PRR2, and Pyk2 super-mutant treated mice. FIG. 8G. Metastatic colonies: quantification of colonies from 1:10 dilution of dissociated lung cells. Each colony was originated from one lung metastatic cell. n=8 (scrambled), n=8 (Pyk2-PRR2), n=6 (Pyk2 super-mutant) mice per group. *P<0.05 by one-way ANOVA followed by Tukey's post-hoc test. Error bars represent SEM.

DETAILED DESCRIPTION OF THE INVENTION

Figure 1A:
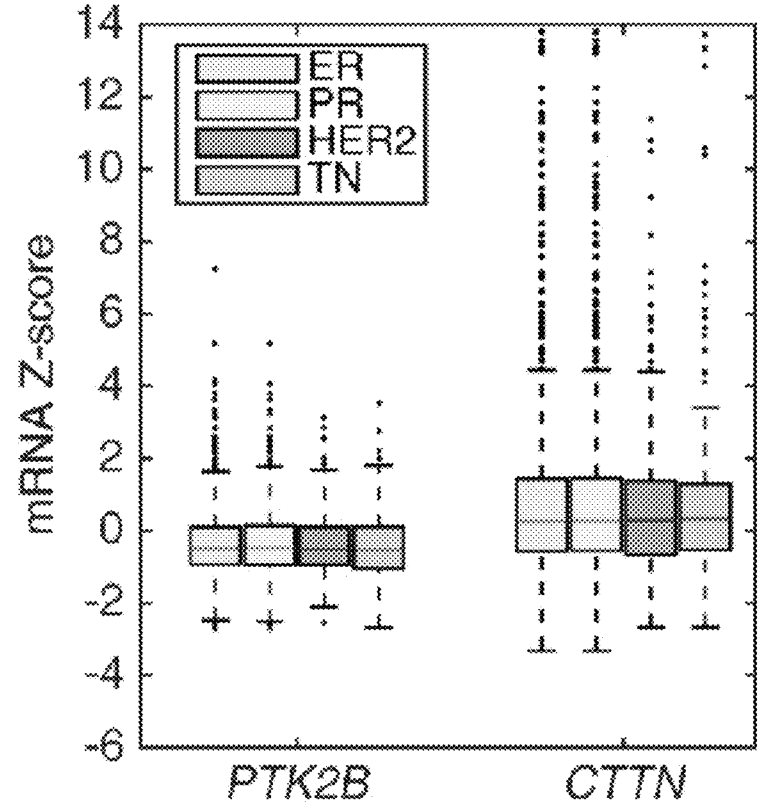
FIGS. 1A-1F show that increased expression of Pyk2 and cortactin is associated with breast cancer metastasis and poor patient prognosis.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Despite the high significance of cortactin for invadopodia-mediated tumor cell invasiveness and subsequent cancer metastasis, the design of a specific cortactin inhibitor has been challenging. Research to date has focused on disruption of the upstream signaling pathway EGFR-Src-Arg-cortactin or inhibition of cortactin protein-protein interactions. Indeed, inhibition of EGFR or Src suppresses invadopodia-mediated invasiveness of head-and-neck squamous cell carcinoma cell lines (Hayes et al. Ableson kinases negatively regulate invadopodia function and invasion in head and neck squamous cell carcinoma by inhibiting an HB-EGF autocrine loop. Oncogene 2013; 32: 4766-4777), while knockdown or selective inhibition of Arg kinase block in vivo breast cancer metastasis (Gil-Henn et al. Arg/Abl2 promotes invasion and attenuates proliferation of breast cancer in vivo. Oncogene 2013; 32: 2622-2630; Meirson et al. Targeting invadopodia-mediated breast cancer metastasis by using ABL kinase inhibitors. Oncotarget 2018; 9: 22158-22183). Also, inhibition of the interaction between the ARF-GAP AMAP1 and cortactin by an AMAP1-derived peptide blocked tumor metastasis and angiogenesis (Hashimoto et al. Targeting AMAP1 and cortactin binding bearing an atypical Src homology 3/proline interface for prevention of breast cancer invasion and metastasis. *Proc Natl Acad Sci USA* 2006; 103: 7036-7041; Hashimoto et al. GEP100-Arf6-AMAP1-cortactin pathway frequently used in cancer invasion is activated by VEGFR2 to promote angiogenesis. *PLoS One* 2011; 6: e23359).

The inventors have previously identified cortactin as a potential substrate of Pyk2 in invadopodia, by using high-throughput protein arrays combined with bioinformatics analysis. Pyk2 was found to bind cortactin via its second proline-rich region (PRR2) at invadopodia of invasive breast cancer cells, where it mediates EGF-induced phosphorylation both directly and indirectly via Src-mediated Arg activation, leading to free actin barbed end generation and subsequent actin polymerization in invadopodia, ECM degradation, and consequent tumor cell invasion (Genna et al., Pyk2 and FAK differentially regulate invadopodia formation and function in breast cancer cells. *J Cell Biol* 2018; 217: 375-395).

In the present invention, the inventors have designed a cell-permeable peptide including the second proline-rich region of Pyk2 (Pyk2-PRR2), with the idea that this peptide may be used to inhibit metastasis by competing with the native Pyk2 on binding to cortactin. This idea was based, inter alia, on an in silico analysis showing that the combined effect of PTK2B (the Pyk2 encoding gene) and CTTN (the cortactin encoding gene) overexpression considerably reduced distant metastasis free survival (DMFS) estimates, suggesting that Pyk2 and cortactin act synergistically to promote breast cancer metastasis (Example 1).

The inventors further demonstrated that the Pyk2-PRR2 peptide inhibits spontaneous lung metastasis in a xenograft mouse model by suppressing invadopodia-mediated invasiveness of breast tumor cells (Example 2). Additionally, the Pyk2-PRR2 peptide was shown to suppress motility of breast cancer cells in extracellular matrix, and specifically matrix metalloproteinase (MMP)-dependent 3D invasiveness of breast tumor cells, in an in vitro tissue culture model (Example 3). Additional examples show that the Pyk2-PRR2 peptide inhibits the interaction between Pyk2 and cortactin (Example 4), as well as inhibiting cortactin tyrosine phosphorylation (Example 5), thereby regulating the maturation and functional activation of invadopodia, and inhibiting invadopodium maturation and function in breast tumor cells.

The interaction of the Pyk2-PRR2 peptide with the SH3 domain of cortactin was mapped by analyzing the three-dimensional structure of this complex using nuclear magnetic resonance (NMR) (Example 6), identifying specific amino acids important for the interaction. Finally, a mutant peptide was prepared by modifying specific positions in the Pyk2-PRR2 peptide based on the 3D analysis, showing that the inhibiting effect is lost (Example 7).

The Pyk2-PRR2 Peptide

In some embodiments, the present invention provides an isolated Pyk2-derived peptide including a consensus proline-rich region 2 (PRR2) sequence, wherein the consensus PRR2 sequence is PxxPx(R/K)P(K/R)(Y/W/F) in which "x" stands for any amino acid; and the peptide is capable of inhibiting metastasis by binding to a Src homology 3 (SH3) domain of cortactin.

The term "isolated peptide" means that the peptide of the invention does not encompass a natural peptide, if such a peptide even exists, functioning in its natural environment. It is also clarified that the term "isolated" does not mean that the peptide is necessarily obtained by isolating it from a cell (but it could be). Additionally, the term "isolated" does not preclude the peptide from being attached or conjugated to additional elements (including amino acid sequences), as further mentioned below.

Proline-rich tyrosine kinase 2 (Pyk2), encoded by the PTK2B gene, is a cytoplasmic protein tyrosine kinase involved in calcium-induced regulation of ion channels and activation of MAP kinase signaling pathway. It contains three proline-rich domains, two of them, proline-rich region 2 ($^{713}$PPPKPSRP$^{720}$, PRR2, (SEQ ID NO: 26), positions in UniProt accession No. Q14289), and proline-rich region 3 ($^{855}$PPQKPPRL$^{862}$, PRR3, (SEQ ID NO: 27)) are involved in Src homology domain 3 (SH3)-mediated protein-protein interactions.

The consensus PRR2 sequence of PxxPx(R/K)P(K/R)(Y/W/F), corresponding to the amino acids at positions 714-722 of the human Pyk2 sequence (UniProt Accession No. Q14289), is based on the below examples, which define the amino acids important for interaction with the cortactin SH3 domain both by an analysis of the complex structure and by testing mutant peptides. The cortactin SH3 domain is between amino acids 495-542 of the cortactin protein.

Figure 6A:
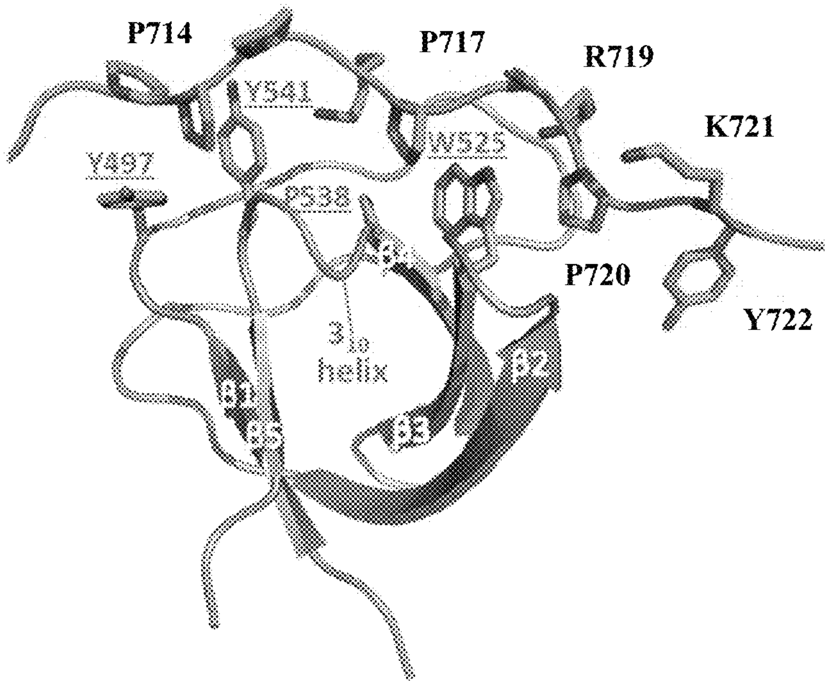
FIGS. 6A-6D show the structure of the cortactin-SH3: Pyk2-PRR2 complex.

The analysis presented in Example 6 shows the importance of positions P714, P717, P720, K721, and Y722 to binding the cortactin SH3 domain. These amino acids were modified in the super mutant (SEQ ID NO: 3: TAFQEPAPKASQAQYRPPP) and in a mutant carrying a Y722A substitution (SEQ ID NO: 5), and were shown to reduce or abolish the inhibiting effect of the peptide. Additionally, a deletion of amino acids 720-726 (SEQ ID NO: 6) demonstrated a 27-fold loss of affinity (FIG. 6D).

The amino acids are indicated herein by the amino acid one letter code:

TABLE 1 amino acids one letter code

| Name | Code |
|---|---|
| Alanine | A |
| Arginine | R |

TABLE 1-continued amino acids one letter code

| Name | Code |
|---|---|
| Asparagine | N |
| Aspartic Acid | D |
| Cysteine | C |
| Glutamic Acid | E |
| Glutamine | Q |
| Glycine | G |
| Histidine | H |
| Isoleucine | I |
| Any amino acid | X |
| Leucine | L |
| Lysine | K |
| Methionine | M |
| Proline | P |
| Phenylalanine | F |
| Serine | S |
| Threonine | T |
| Tryptophan | W |
| Tyrosine | Y |
| Valine | V |

In some embodiments, the consensus PRR2 sequence is selected from the group consisting of PxxPxRPKY (SEQ ID NO: 12), PxxPxRPRY (SEQ ID NO: 13), PxxPxKPRY (SEQ ID NO: 14), PxxPxKPKY (SEQ ID NO: 15), PxxPxRPKW (SEQ ID NO: 16), PxxPxRPRW (SEQ ID NO: 17), PxxPxKPRW (SEQ ID NO: 18), PxxPxKPKW (SEQ ID NO: 19), PxxPxRPKF (SEQ ID NO: 20), PxxPxRPRF (SEQ ID NO: 21), PxxPxKPRF (SEQ ID NO: 22), and PxxPxKPKF (SEQ ID NO: 23). In some embodiments, the consensus PRR2 sequence is PxxPxRPKY (SEQ ID NO: 12).

The positions marked with an "x" may be any amino acid. In some embodiments, at least one of the positions marked with "x" is proline. In some embodiments, at least one of the positions marked with "x" is a basic amino acid.

The term "basic amino acid", as defined herein, relates to the amino acids arginine or lysine.

In some embodiments, the consensus PRR2 sequence is PPKPSRPKY (SEQ ID NO: 24).

In some embodiments, the peptide further includes additional sequence at the amino-terminal side of the consensus PRR2 sequence. In some embodiments, the peptide further includes additional sequence at the carboxy-terminal side of the consensus PRR2 sequence. In some embodiments, the additional sequence comprises sequence derived from the Pyk2 protein.

The term "derived from", as used herein, means that a first sequence derived from a second sequence has at least a certain level of sequence identity to the second sequence it is said to be derived from. In some embodiments, the certain level of sequence identity is at least about 70%, 75%, 80%, 85%, 90%, 95%, or 99%.

In some embodiments, the peptide includes at least one additional proline outside of the consensus sequence. In some embodiments, the at least one additional proline is N-terminal to the consensus sequence. In some embodiments, the at least one additional proline is C-terminal to the consensus sequence.

In some embodiments, the peptide includes at least one additional basic amino acid outside of the consensus sequence. In some embodiments, the at least one basic amino acid is N-terminal to the consensus sequence. In some embodiments, the at least one basic amino acid is C-terminal to the consensus sequence.

In some embodiments, the peptide includes at least one amino acid selected from the group consisting of glycine, methionine, threonine, alanine, or cysteine outside of the consensus sequence, for stabilizing the protein. In some embodiments, the peptide includes at least one amino acid selected from the group consisting of glycine, methionine, threonine, alanine, or cysteine N-terminal to the consensus sequence.

In some embodiments, the peptide includes at least one tag sequence. In some embodiments, the at least one tag sequence is N-terminal to the consensus sequence. In some embodiments, the at least one tag sequence is C-terminal to the consensus sequence.

The term "tag sequence", as used herein, relates to a short sequence (typically several amino acids, such as less than 10 amino acids) which is added to a peptide or a protein sequence for a certain purpose such as for easy detection, or for targeting.

In some embodiments, the tag sequence is selected from the group consisting of an HIV-TAT tag, which is typically used for increasing permeability into cells; and a HAIYPRH (Tf tag) used for targeting the peptide to cancer cells.

It is appreciated that the peptide may further include any additional elements or modifications, including protein/peptide fusion, which may be added for any reason, including to increase stability, or help delivery or targeting.

In some embodiments, the peptide is capped at the N-terminal end, the C-terminal end, or both, for protection and stability. The cap may be any suitable cap, including, e.g., an Ac cap at the N-terminal end, or an amino cap at the C-terminal end.

In some embodiments, the peptide includes a sequence at least 70%, 75%, 80%, 85%, 90%, 95%, or 99% identical to a sequence of Pyk2. In some embodiments, the peptide sequence is at least 70%, 75%, 80%, 85%, 90%, 95%, or 99% identical to a sequence of Pyk2.

In some embodiments, the peptide includes a sequence at least 70%, 75%, 80%, 85%, 90%, 95%, or 99% identical to a sequence including the second proline-rich region of Pyk2. In some embodiments, the peptide sequence is at least 70%, 75%, 80%, 85%, 90%, 95%, or 99% identical to a sequence including the second proline-rich region of Pyk2.

In some embodiments, the Pyk2 is a human Pyk2.

In some embodiments, the peptide does not include a complete Pyk2 protein sequence. In some embodiments, the peptide does not include a proline-rich region 3 (PRR3) sequence of a Pyk2 protein. In some embodiments, the peptide does not include any functional Pyk2 region sequence except for the PRR2 sequence.

In some embodiments, the peptide includes a sequence at least 70%, 75%, 80%, 85%, 90%, 95%, or 99% identical to the sequence set forth in SEQ ID NO: 1, corresponding to the amino acids at positions 708-726 of the human Pyk2 protein sequence (UniProt accession Q14289). In some embodiments, the peptide sequence is at least 70%, 75%, 80%, 85%, 90%, 95%, or 99% identical to the sequence set forth in SEQ ID NO: 1. In some embodiments, the peptide sequence includes SEQ ID NO: 1.

In some embodiments, the peptide has a length of about 9-100, 9-50, 10-30, or 15-25 amino acids. In some embodiments, the peptide has a length of about 15, 16, 17, 18, 19, 20, 21, 22, 23, 24, or 25 amino acids.

Peptide therapeutic agents also pose challenges, such as proteolysis, rapid renal clearance, low oral bioavailability, and membrane permeability, these can be effectively overcome using peptidomimetic compounds involving D- or non-proteogenic amino acids, various cyclization approaches, and tailored delivery methods. Other options for stabilization including adding prolines or non-native amino acids.

Since there is a possibility that such modifications may affect the interaction of the peptide with the cortactin SH3 domain, such modifications may be limited to amino acids which are outside of the consensus region. Non-limiting examples for non-conventional or modified amino acids include D-amino acids, and α-substituted amino acids.

In some embodiments, the peptide is a cyclic peptide. In some embodiments, the peptide includes at least one non-conventional and/or at least one modified amino acid. In some embodiments, the peptide includes at least one non-conventional and/or at least one modified amino acid outside of the consensus sequence. In some embodiments, the non-conventional amino acid is a D-amino acid.

In some embodiments, the peptide has a sequence as set forth in SEQ ID NO: 9: TAFQEPPPKPSRPKYRPPP, bold denoting a D-amino acids.

As shown in Example 2, the Pyk2-PRR peptides did not suppress tumor growth, which indicates that the peptides of the invention are most likely specific to metastasis.

Accordingly, in some embodiments, the Pyk2-derived peptide does not inhibit primary tumor growth.

Nucleic Acids Encoding the Peptide

In some embodiments, the present invention provides a nucleic acid including a sequence encoding the Pyk2-derived peptide disclosed herein.

Definitions and embodiments mentioned above and which may be relevant to the nucleic acid embodiments also apply here, and vice versa. Some particularly relevant embodiments may be pointed out or explicitly repeated.

Instead of using the peptide directly, it is conceivable that it may be produced within a cell, by transcription from a nucleic acid template encoding the peptide. To this end, a nucleic acid including a sequence encoding the peptide may be inserted into a suitable expression vector (such as an adenoviral vector, adenovirus-associated vector, or a lentiviral vector) which includes sequences required for expression in mammalian cells (such as promoter, terminator, regulatory elements, etc.), for expression in a desired cell. The vector may be targeted to cancer cells for expressing the peptide.

Pharmaceutical Compositions

In some embodiments, the present invention provides a pharmaceutical composition including the isolated Pyk2-derived peptide disclosed herein and a pharmaceutically-acceptable carrier.

Definitions and embodiments mentioned above and which may be relevant to the pharmaceutical composition embodiments also apply here, and vice versa. Some particularly relevant embodiments may be pointed out or explicitly repeated.

The pharmaceutical composition may include any ingredients suitable for delivery of the peptide of the invention, including any suitable form of encapsulation, such as nanoparticles or microparticles, liposomes, fusion proteins, or other lipid or protein or other molecules carriers. The pharmaceutical compositions may further include targeting reagents, for targeting to a desired tissue or cell.

In some embodiments, the pharmaceutically acceptable carrier is a buffer, diluent, adjuvant, excipient, or vehicle suitable for administration with the peptide of the invention. In some embodiments, the pharmaceutically acceptable carrier may be suitable for intravenous infusion. In some embodiments, the pharmaceutically acceptable carrier may be suitable as a cryoprotectant. In some exemplary embodiments, the carrier may be DMSO (for example, at about 10%). In some embodiments, the pharmaceutically acceptable carrier may include a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

Methods of Treatment

In some embodiments, the present invention provides a method of treating a cancer in a subject, the method including administering to the subject a therapeutically-effective dose of the isolated Pyk2-derived peptide disclosed herein.

Definitions and embodiments mentioned above and which may be relevant to the method of treatment embodiments also apply here, and vice versa. Some particularly relevant embodiments may be pointed out or explicitly repeated.

In some embodiments, the present invention provides a method of preventing or inhibiting cancer metastasis in a subject, the method including administering to the subject a therapeutically-effective dose of the isolated Pyk2-derived peptide disclosed herein.

In some embodiments, the present invention provides a method of preventing or inhibiting cancer invasion in a subject, the method including administering to the subject a therapeutically-effective dose of the isolated Pyk2-derived peptide disclosed herein.

The term "treating", as used herein, refers to means of obtaining a desired physiological effect, in this case, ameliorating the symptoms of the cancer and enhancing recovery by partially or completely inhibiting or blocking metastasis of the cancer. In some embodiments, the treating includes preventing and/or inhibiting cancer invasion and/or metastasis.

The term "cancer invasion", as used herein, relates to the process in which cancer cells extend beyond the organ or tissue in which the cancer originated and penetrate neighboring tissues or organs. This process generally takes place by migration of cancer cells through the extracellular matrix into surrounding tissues.

The term "cancer metastasis", as used herein, relates to the process in which the cancer cells spread through the circulatory system or the lymphatic system to more distant locations than neighboring tissues. In solid cancers which are not in the circulatory or the lymphatic systems, metastasis follows invasion.

The term "inhibiting", as used herein with respect to cancer invasion or metastasis, relates to delaying their appearance or reducing their amount relative to the expected rate or development of invasion or metastasis under similar conditions.

The term "preventing", as used herein, relates to preventing appearance of cancer invasion or metastasis from the treated cancer completely.

The term "therapeutically effective dose" as used herein means an amount of the peptide that will elicit the desired biological or medical effect. The amount must be effective to achieve the desired therapeutic effect as described above, depending inter alia on the type and severity of the cancer and the treatment regime. The therapeutically effective dose is typically determined in appropriately designed clinical trials (dose range studies) and the person skilled in the art will know how to properly conduct such trials to determine the effective amount.

The administering may be by any method or route suitable for treating the cancer. The administration regimen may be determined by a physician based on the condition of the subject.

The administration may be a systemic or a local administration. Non-limiting examples for administration routes include intravenous, intraarterial, intraperitoneal, intramuscular, subcutaneous, oral, sublingual, enteral, intranasal, buccal, vaginal, rectal, intraocular, intrathecal, topical, transdermal, and intradermal administration.

In some embodiments, the route of administration is selected from the group consisting of intravenous, subcutaneous, intramuscular, intratumoral, intraperitoneal, intranasal, intratumoral, and topical administration.

The added benefit of the peptide of the invention may also be important in view of that cancer treatments have sometimes been shown to have an adverse effect of inducing metastasis.

This further emphasizes the importance of a treatment for preventing or inhibiting invasion and metastasis in addition to any cancer treatment that is directed against the primary tumor. Treating the subject early with a combination of the cancer treatment and the peptide of the invention may have a complementary effect of both treating the primary tumor and preventing metastasis.

Accordingly, the peptide of the invention may be administered to the subject in combination with an anti-cancer treatment, for completely eradicating the cancer. The term "in combination", as used herein, means as part of the same treatment and not necessarily at the same time. The peptide of the invention may be administered before, after, or at the same time as the anti-cancer treatment, or as part of a regimen which includes both the peptide and the anti-cancer treatment.

Additionally, in some situations the peptide of the invention may be used as part of a palliative treatment, for prolonging life or for enhancing quality of life, without necessarily also administering anti-cancer treatment.

Accordingly, in some embodiments, the method further includes administering to the subject an anti-cancer treatment.

In some embodiments, the present invention provides a method of treating a cancer in a subject, including administering to the subject a combination of the isolated Pyk2-derived peptide disclosed herein and an anti-cancer treatment.

Non-limiting examples for anti-cancer treatments include chemotherapy, immunotherapy, radiotherapy, etc.

As noted above, there may be an advantage to treating with the peptide at an early stage, even before the appearance of invasion or metastasis. However, there is also benefit in treating even after invasion and metastasis have occurred, to limit the level of metastasis and help contain the disease, thereby increasing the efficacy of anti-cancer treatments.

In some embodiments, the cancer is invasive. In some embodiments, the cancer is not invasive. In some embodiments, the cancer is metastatic. In some embodiments, the cancer is not metastatic.

In some embodiments, the cancer does not include metastases.

In some embodiments, the cancer includes metastases.

In some embodiments, the cancer includes invadopodia.

In some embodiments, the cancer is selected from the group consisting of breast cancer, pancreatic cancer, head and neck cancer, prostate cancer, fibrosarcoma, and melanoma.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a ratio, and the like, is meant to encompass variations of 10% of the indicated value, as such variations are also suitable to perform the disclosed invention. Any numerical values appearing in the application are intended to be construed as if preceded by "about", unless indicated otherwise.

While certain embodiments of the invention have been illustrated and described, it will be clear that the invention is not limited to the embodiments described herein. Numerous modifications, changes, variations, substitutions, and equivalents will be apparent to those skilled in the art without departing from the spirit and scope of the present invention as described by the claims, which follow.

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

EXAMPLES

Materials and Methods

Peptides

The positions indicated in Table 2 correspond to UniProt accession No. Q14289. In SEQ ID Nos: 1-6 bold indicates consensus positions, and substitutions are underlined.

Peptides were synthesized by GL Biochem (Shanghai, China). In all cellular biology and in vivo experiments, peptides contained the HIV-TAT sequence at their C-termini (SEQ ID NO: 11) to increase their permeability into cells. For invadopodia, matrix degradation, 2D motility assays, and 3D invasion assays, peptides containing the TAT sequence were conjugated to FITC at their C-termini to track their delivery into cells.

The assays of the present disclosure were conducted using Pyk2-PRR2 (SEQ ID NO: 1), which corresponds to positions 708-726 of UniProt accession No. Q14289 for human Pyk2. Additional assays that were conducted by adding a Tf-tag (HAIYPRH, SEQ ID NO: 10), which targets sequences to transferrin receptors overexpressed in cancer cells, either N-terminal (HAIYPRHTAFQEPPPKPSRPKYRPPP, SEQ ID NO: 7) or C-terminal (TAFQEPPPKPSRPKYRPPPHRPYIAH, SEQ ID NO:8) to the Pyk2-PRR2 sequence.

It is also possible to use sequences wherein D-amino acids are used, such as TAFQEPPPKPSRPKYRPPP (SEQ ID NO: 9, bold denotes a d-amino), as described above.

Some of the sequences used included a cap for protection at the N-terminus (Ac cap, used for the peptide containing a C-terminal Tf-tag and for the sequence containing D-amino acids), the C-terminus ($NH_2$ cap used for the peptide containing an N-terminal Tf-tag and for the sequence containing D-amino acids) or both.

Cell Culture

MDA-MB-231 human breast adenocarcinoma cells and 4T1 mouse mammary tumor cells were obtained from the American Type Culture Collection. MDA-MB-231 were cultured in DMEM/10% FBS, and 4T1 cells were cultured

TABLE 2 peptide sequences

| Name | SEQ | Pyk2 Positions | sequence |
|---|---|---|---|
| Pyk2-PRR2 | 1 | 708-726 | TAFQEP**P**PK**P**S**RPKY**RPPP |
| Pyk2-PRR3 | 2 | 851-866 | EFTGPPQKPPRLGAQS |
| Pyk2 super-mutant | 3 | 708-726 (P714A, P717A, R719Q, P720A, K721Q) | TAFQEP**A**PK**A**S **QAQY**RPPP |
| Control | 4 | | PEPYPTPAPFP KKQRPRPS |
| Pyk2-PRR2-Y722A mutant | 5 | 708-726 (Y722A) | TAFQEP**P**PK**P**S **RPKA**RPPP |
| Pyk2-PRR2 del | 6 | 708-719 | TAFQEP**P**PK**P**S**R** |
| Tf-tag-Pyk2-PRR2 | 7 | | HAIYPRHTAFQEP PPKPSRPKYRPPP |
| Pyk2-PRR2-Tf-tag | 8 | | TAFQEPPPKPSRP KYRPPPHRPYIAH |
| Pyk2-PRR2 with D-aa | 9 | | **TAFQ**EPPPKPSRPK YR**PPP**-(bold denotes D-amino acids) |
| Tf-tag | 10 | | HAIYPRH |
| HIV-TAT tag | 11 | | GRKKRRQRRRK |

in RPMI 1640/10% FBS. MDA-MB-231 cells stably expressing cortactin-TagRFP were previously described (Oser et al. Specific tyrosine phosphorylation sites on cortactin regulate Nck1-dependent actin polymerization in invadopodia. *J Cell Sci* 2010; 123: 3662-3673).

Mouse Xenograft Model

All experimental procedures were conducted following the Federation of Laboratory Animal Science Association (FELSA) and were approved by the Bar-Ilan University animal use and care committee. Mouse xenograft tumors were generated by injecting $10^6$ 4T1 cells resuspended in 20% collagen I (BD Biosciences, Franklin Lakes, NJ, USA) in PBS into the lower-left mammary gland of 8-week-old BALB/c female mice. Twelve days following injection, when tumors reached the size of 100 $mm^3$, mice were treated by intravenous injection with 10 mg/kg of control scrambled, Pyk2-PRR2, Pyk2-PRR3, or Pyk2 super-mutant peptides once a day for eight days.

Spontaneous Lung Metastasis Clonogenic Assay

4T1 cells have intrinsic resistance to 6-thioguanine, which enables precise quantification of metastatic cells, even when they are disseminated at sub-microscopic levels at distant organs, upon excision and digestion of selected organs. The clonogenic assay is based on a principle by which one colony represents one metastatic cell. Briefly, spontaneous lung metastasis was measured in BALB/c mice bearing orthotopic 4T1 tumors of equal size (1-1.2 cm in diameter). Lungs were excised and minced and plated in RPMI/10% FBS in the presence of 6-thioguanine to select for tumor cells only. Cells were plated in a 5% CO2 incubator at 37 °C for 14 days to form 4T1 colonies. On day 14 after plating, the medium was removed from dishes, and colonies were fixed in 4% paraformaldehyde for one hour at room temperature. Colonies were then stained in 2% crystal violet solution and thoroughly washed with PBS. Plates were allowed to air dry, and colonies in each plate were quantified.

Proteogenomic Analysis

Data from two cohorts of 1,080 and 825 breast invasive carcinoma samples was obtained from The Cancer Genome Atlas (TCGA at the National Institutes of Health) and analyzed with cBioPortal tools using MATLAB. The analyzed datasets contain mRNA-seq expression Z-scores (RNA-Seq V2 RSEM) and Agilent microarray mRNA Z-scores computed as the relative expression of an individual gene and tumor to the expression distribution of all samples that are diploid for the gene. Putative copy number alteration (GISTIC) was collected from both cohorts. GISTIC is an algorithm that attempts to identify significantly altered regions of amplification or deletion and uses discrete copy number calls: homozygous deletion; heterozygous loss; neutral; gain; high amplification. Breast cancer samples are annotated with OS and/or DFS time and censorship status. Samples were split into high and low expressing groups based upon median mRNA expression Z-scores. Associations between Z-scores and patient survival (DFS and OS) were assessed by Kaplan-Meier time-event curves and Mantel-Haenszel hazard ratios using an implementation of Kaplan-Meier log rank testing from MATLAB Exchange. All statistical tests were two-sided. Mass-spectrometry based proteomic characterization of 102 breast cancer tumor samples [4] was obtained from the Clinical Proteomic Tumor Analysis Consortium (CPTAC) Data Portal (at Georgetown university) with cBioPortal using MATLAB. For each protein target, Z-scores were determined and associated P-values were calculated across all samples.

Distant Metastasis-Free Survival Analysis

Microarray datasets with Distant Metastasis-Free Survival (DMFS) annotation were obtained from the NCBI Gene Expression Omnibus (GEO) data repository of high-throughput microarray experimental data. The meta-cohort dataset comprised of 1,650 tumor expression profiles of primary invasive breast cancer based on the Affymetrix U133 GeneChip microarray platform. Queried transcripts included 22,283 probe sets common to all microarrays in all study populations. Assembly of the datasets was performed using MATLAB (The Mathworks, Inc.) and GEO series (GSE) files were extracted via GEO accessions GSE11121, GSE25055, GSE7390, GSE25065, GSE17705, GSE12093, GSE1456, GSE5327 and GSE45255. The datasets have been retrieved with uniform normalization of probe intensities with MAS 5.0 using global scaling with a trimmed mean target intensity of each array arbitrary set to 600. Cross-population batch effects were corrected using Z-score transformation. The tumor profiles represent primary invasive breast tumors sampled at the time of surgical resection, annotated with DMFS time and censorship status Patient samples were split into high and low expressing groups based upon median gene expression. Associations between normalized gene expression and patient survival (DMFS) were assessed by Kaplan-Meier time-event curves and Mantel-Haenszel hazard ratios using an implementation of Kaplan-Meier log rank testing from MATLAB Exchange. All statistical tests were two-sided. The synergy index (SI) was calculated as a means of evaluating additive interaction. The synergy index can be interpreted as the excess risk from overexpression of both genes relative to the risk of overexpression of the genes separately. SI of 1 indicates no synergism, and an SI>1 indicates synergistic interaction between the two genes.

Antibodies

For immunofluorescence, anti-cortactin (ab-33333) and anti-PCNA (ab18197) were obtained from Abcam (Cambridge, UK); anti-Arp2 (N1C3) was obtained from GeneTex (Irvine, CA, USA); anti-Tks5 (SH3 #4; 09-268) was obtained from EMD Millipore (Burlington, MA, USA); anti-pY421-cortactin (C0739) was obtained from Sigma-Aldrich (St. Louis, MO, USA); anti-pY402-Pyk2 (44-618G) was obtained from Thermo Fisher Scientific (Waltham, MA, USA); anti-CD31 (550274) was obtained from BD Biosciences (Franklin Lakes, NJ, USA); anti-cleaved caspase 3 (Asp175; 9961) was obtained from Cell Signaling Technology (Danvers, MA); Rhodamine-labelled phalloidin and Alexa Fluor-conjugated secondary antibodies were obtained from Molecular Probes (Thermo Fisher Scientific). For immunoblotting, anti-cortactin (clone 4F111; 05-180) was obtained from EMD Millipore; anti-3-actin (clone AC-15; A5441) was obtained from Sigma-Aldrich. Secondary antibodies (goat anti-mouse 680LT and goat anti-rabbit 800CW) were obtained from LI-COR Biosciences (Lincoln, NE, USA).

Metastasis Assay in a Xenograft Mouse Model/Tumor Immunohistochemistry

4T1 cells were injected into the mammary fat pad of 8-week-old BALB/c female mice and allowed to grow for 12 days. On day 13 following injection, mice were treated by intraperitoneal injection with scrambled control, Pyk2-PRR2, or Pyk2-PRR3 peptides once a day for eight days. Mice bearing 4T1 mammary tumors were then sacrificed, and tumors or lungs were excised, fixed in 4% paraformaldehyde overnight, washed for 1 hour in cold PBS, and dehydrated overnight in 30% sucrose. Next, tissue was embedded in OCT, and 5 m thick cryostat sections were placed on silane-coated slides and dried at room temperature followed by permeabilization with 0.1% Triton X-100 for 15 min and blocking in 1% BSA and 1% FBS for 1 hour at room temperature. Samples were then incubated overnight at 4 °C with the indicated primary antibodies, washed, and incubated with the appropriate secondary antibodies. Nuclei were counterstained with 4',6-diamino-2-phenylindole (DAPI). Tissue was imaged using an inverted laser scanning confocal microscope (Zeiss LSM780; 63×, NA 1.4, oil objective, ZEN black edition acquisition software) (Oberkochen, Germany). For all assays results were based on n=7-10 mice/tumors per group.

Cell Permeability Assay

MDA-MB-231 were plated and allowed to adhere for 4 h. Adherent cells were incubated with 0.1 or 1 M Pyk2 peptides containing HIV-TAT sequences and conjugated to FITC for 20 min, 8 h, and 24 h. At the end of the incubation time, the cells were fixed and analyzed by fluorescence microscopy.

XTT Assay

MDA-MB-231 cells were resuspended to reach a concentration of 5,000 cells/well and were seeded in triplicates in flat bottom 96 well microtiter plates. Following overnight incubation at 37 °C in a tissue culture incubator, Pyk2-PRR2, Pyk2-PRR3, or a scrambled control peptide was added to a final concentration of 0.1, 1, 5, or 10 μM, and cells were followed every 24 h for 96 h in total. Activated XTT solution was prepared according to the manufacturer's instructions (Biological Industries, Beit Haemek, Israel) and added to the cells for 4 h. Two filters were used, the specific absorbance filter at 475 nm and the non-specific absorbance filter at 660 nm. Specific absorbance was calculated using the formula: A 475 nm (test)−A475 nm (blank)−A660 nm (test).

2D Single-Cell Random Migration Assay

The 2D single-cell random migration assay was performed as previously described in Genna et al. Pyk2 and FAK differentially regulate invadopodia formation and function in breast cancer cells. *J Cell Biol* 2018; 217: 375-395. In brief, 6-well microtiter plates were coated with 10 g/ml fibronectin and blocked with 1% denatured BSA. Peptide pre-treated cells were plated at 20,000 cells/well in DMEM/10% FBS containing peptides and allowed to adhere for 12-16 h. Plates were placed in a 37 °C heated chamber, and images were collected using the IncuCyte® Zoom platform (Essen Bioscience, Ann Arbor, MI, USA; 20×, NA 0.60, air objective). Phase images were collected every one hour for a total of 12 h using the IncuCyte® acquisition software. Trajectory plots, accumulated distance (total cell path length), Euclidean distance (the shortest distance between the starting point and endpoint of migration), and velocity were calculated using the chemotaxis and migration tool (ibidi GMBH, Gräfelfing, Germany).

3D Scratch Wound Assay

The 3D scratch wound assay was performed as described in Meirson et al. Targeting invadopodia-mediated breast cancer metastasis by using ABL kinase inhibitors. Oncotarget 2018; 9: 22158-22183. Briefly, 96 well Image Lock microtiter plates (Essen Bioscience) were coated with 100 g/ml Matrigel (cat #354234; Corning, New-York, NY, USA). Following overnight incubation at 37 °C, MDA-MB-231 cells were plated at a final concentration of 350,000 cells/ml and allowed to adhere for 12-16 h in the presence of Pyk2-PRR or control peptides. Following wounding of the bottom Matrigel-cells layer, a top layer of Matrigel was added to a final concentration of 2 mg/ml and allowed to polymerize for 30 min at 37 °C. Pyk2-PRR or control scrambled peptides were then added again in DMEM/10% FBS to a final concentration of 0.1, 1, or 5 μM, with or without the MMP inhibitor GM6001 (25 μM). Plates were placed in a 37 °C heated chamber, and images were collected using the IncuCyte® Zoom platform (Essen Bioscience; 20×, NA 0.60, air objective). Phase images were collected every one hour for a total of 12 h using the IncuCyte® acquisition software.

Acceptor Photobleaching FRET Assay

Acceptor photobleaching experiments were performed as described in Genna et al., 2018 (supra). In brief, cortactin-TagRFP MDA-MB-231 cells were plated on Alexa 405 gelatin in a medium containing Pyk2-PRR or scrambled control peptides at 0.1, 1, and 5 μM concentration, fixed, and immunostained with pY402-Pyk2/Alexa Fluor 488-goat anti-rabbit (donor) and cortactin/Alexa Fluor 555-goat anti-mouse (acceptor). As a control, cells were stained with Tks5/Alexa Fluor 488-goat anti-rabbit (donor) and cortactin/Alexa Fluor 555-goat anti-mouse (acceptor). Co-localization of cortactin with degradation holes in Alexa 405-labeled gelatin was used to identify mature degrading invadopodia. For all FRET experiments, cells were imaged in PBS at room temperature on a laser-scanning inverted confocal microscope (Zeiss LSM780; 60×, NA 1.4, oil objective). A region of interest surrounding invadopodia was bleached using 100% 561-nm laser power (acceptor channel), and images were acquired in both the 488 nm and the 561 nm channels before and after bleaching. FRET efficiency was calculated as the E=1−(donor pre/donor post) in background-subtracted images and was corrected for fluctuations in laser power and donor bleaching in ImageJ.

Invadopodium Precursor Formation Assay

The invadopodium precursor formation assay was performed as described in Genna et al., 2018 (supra). Briefly, gelatin was conjugated to Alexa 405 dye (Thermo Fisher Scientific). MatTek dishes were treated with 1 N HCl and coated with 50 g/ml poly-L-lysine. A 0.2% gelatin solution was prepared in PBS, and a 1:20 mixture of Alexa 405-labeled gelatin/unlabeled gelatin was warmed to 37 °C before addition to the poly-L-lysine coated plates. Gelatin was cross-linked with 0.01% glutaraldehyde followed by quenching with 5 mg/ml sodium borohydride. 125,000 MDA-MB-231 cells were plated on Alexa 405-labeled gelatin plates in the presence of 0.1, 1, or 5 μM of Pyk2-PRR peptides or scrambled control for 4 h. At the end of incubation, cells were fixed in 3.7% paraformaldehyde, permeabilized with 0.1% Triton X-100, blocked with 1% FBS, 1% BSA in PBS, and labeled with anti-Tks5 and anti-cortactin. Images were acquired using an inverted fluorescent microscope (Leica AF6000; 63×, NA 1.4, oil objective, Leica LAS AF acquisition software) (Wetzlar, Germany) equipped with an ORCA-Flash 4.0 V2 digital CMOS camera (Hamamatsu Photonics, Shizuoka, Japan). Invadopodium precursors were identified as Tks5- and cortactin-rich punctate structures found in the ventral plane of the cell that do not co-localize with degradation areas, whereas mature invadopodia were identified as Tks5 and cortactin-rich puncta that co-localize with degradation areas at the ventral plane of the cell.

ECM Degradation Assay

The in vitro matrix degradation assay was performed as described in Genna et al., 2018 (supra). Briefly, MatTek dishes were treated with 2.5% gelatin/2.5% sucrose, cross-linked with 0.5% glutaraldehyde, treated with 10 g/ml of fluorescently labeled fibronectin (Alexa 568; Invitrogen, Thermo Fischer Scientific), and then with 1 mg/ml NaBH4 in PBS. 125,000 cells were plated on the fibronectin/gelatin matrix in Pyk2-PRR or control peptides and allowed to degrade for 24 h. Cells were then fixed in 3.7% paraformaldehyde, and random fields were imaged using an inverted fluorescent microscope (Leica AF6000; 40×, NA 1.3, oil objective). ECM degradation was analyzed by quantifying the average degraded area in pixels per field using ImageJ.

Immunofluorescence Analysis of Cortactin Tyrosine Phosphorylation at Invadopodium Precursors Twenty-four hours before each experiment, cells were plated on fibronectin/gelatin unlabeled matrix in the presence of a Pyk2-PRR or control peptides at 0.1, 1, and 5 μM concentration and allowed to attach for eight hours. Cells were then starved in DMEM/0.5% FBS for 16 h in the presence of peptides and stimulated with 2.5 nM EGF for 3 min or left un-stimulated (0 min EGF). Cells were fixed and stained with mouse phospho-specific cortactin antibody (pY421). To image invadopodia Z-plane, focus was on the ventral surface of the cell where the leading edge containing cortactin is focused. The pixels corresponding to invadopodia dots were then analyzed, not the whole cell. The intensity (mean grey value (mgv) minus background) of cortactin-TagRFP and pY421-cortactin at invadopodium precursors was quantified. The pY421-cortactin/cortactin-TagRFP ratio was calculated as a measure of tyrosine-phosphorylated cortactin at cortactin-rich puncta. Data were normalized to resting cells (0 min EGF) and presented as the relative fold change in cortactin tyrosine phosphorylation.

Barbed End Formation Assay

The barbed end assay was performed using biotin-conjugated actin as described in Genna et al., 2018 (supra). In brief, 24 h before each experiment, cells were plated on fibronectin/gelatin unlabeled matrix in the presence of Pyk2-PRR or control peptides at 0.1, 1, or 5 μM concentration and allowed to attach for 8 h. Cells were starved for 16 h in the presence of the peptides and then stimulated with 2.5 nM EGF and permeabilized with a permeabilization buffer (20 mM Hepes, pH 7.5, 138 mM KCl, 4 mM $MgCl_2$, 3 mM EGTA, 0.2 mg/ml saponin, 1 mM ATP, and 1% BSA) containing 0.4 μM biotin-conjugated muscle actin (AB07) (Cytoskeleton Inc., Denver, CO, USA) for 1 min at 37 °C. Cells were fixed in 3.7% paraformaldehyde for 5 min, blocked in PBS containing 1% FBS, 1% BSA, and 3 M un-labeled phalloidin (Molecular Probes, P3457), then labeled with FITC anti-biotin (200-092-211) (Jackson ImmunoResearch Laboratories, West Grove, PA, USA) to visualize barbed ends, and with rhodamine-phalloidin (R415) (Molecular Probes, Eugene, OR, USA) and Arp2 to identify regions of cells rich in invadopodia. The barbed end intensity at invadopodia-rich regions was quantified by measuring mgv at invadopodia-rich areas minus mgv of the background. Data were normalized to the control condition for each experiment.

Expression and Purification of Cortactin-SH3 Domain

The DNA sequence encoding the SH3 domain of the mouse cortactin SH3 domain (GenBank ID U03184; nucleotides1468-1641) was sub-cloned into a pET-28a plasmid (Novagen, Merck) in frame with the cleavable N-terminal 6×His tag. Isotopically labeled cortactin-SH3 for heteronuclear NMR experiments was expressed in transformed *E. coli* BL21 cells (DE3) grown in the presence of kanamycin (50 mg/l) and chloramphenicol (34 mg/l) at 37 °C in M9 minimal medium [13]. For $^{15}N$ ($^{13}C$) labeling the medium contained 1 g/L of $^{15}NH_4Cl$ (4 g/L $^{13}C6$-glucose), and 0.25 g/l of appropriately labeled Celtone Base Powder (Cambridge Isotope Laboratories, Andover, MA) was added. For triple-labeled $^2H$,$^{13}C$, $^{15}N$—SH3, expression began in 100 ml of the above medium grown to an $OD_{600}$ of 0.4-0.5 and gently centrifuged. Pellets were then resuspended in 500 ml filter-sterilized $D_2O$-based $^{15}N$-M9 supplemented with $^2H_7$-$^{13}C_6$-glucose (2 g/l) and DCN-Isogro (0.25 g/l) to reach a final $OD_{600}$ of ~0.1. In both cases cells were then grown at 37 °C and induced with 0.5 mM isopropyl β-D-1-thiogalactopyranoside (IPTG) upon reaching $OD_{600}$~0.8, followed by overnight growth at 27 °C. To purify the SH3 domain, cells were harvested by centrifugation, subjected to a single freeze-thaw cycle, and resuspended in lysis buffer (50 mM NaPi pH 8.0, 300 mM NaCl, 1 mM dithiothreitol (DTT), 100 ml per liter of culture) supplemented with 1 tablet EDTA-free protease inhibitor cocktail (Merck) and benzamidine (5 mM). Cells were lysed by French press, followed by addition of benzamidine (final concentration 10 mM) and phenylmethylsulfonyl fluoride (PMSF, 1 mM), and the lysate was clarified by centrifugation. The supernatant was loaded on a HisTrap HP column (GE Healthcare, Chicago, IL, USA) equilibrated with lysis buffer and the protein eluted through a gradient (Buffer B: 50 mM NaPi pH 8.0, 100 mM NaCl, 300 mM imidazole, 1 mM DTT). To the fraction eluting at ~40% B purified tobacco etch virus (TEV) protease (1:30 mol:mol) was added, and the mixture dialyzed overnight at 4 °C against dialysis buffer (50 mM NaPi at pH 8.0, 100 mM NaCl, 1 mM DTT). The dialysate was brought to a final concentration of ~5 mM imidazole, filtered, and loaded onto a HisTrap column. The collected flowthrough was dialyzed against 20 mM Tris (pH 7.5), 1 mM DTT for 3 h to reach a final concentration of 10 mM NaCl. This fraction was then loaded onto a Q HP Sepharose ion-exchange column (GE Healthcare) and eluted through a gradient at ~45% buffer B (20 mM Tris pH 7.5, 1 M NaCl, 1 mM DTT), flash-frozen and stored at −80 °C.

Preparation of the SH3-PRR2 Complex

Purified SH3 was dialyzed against NMR sample buffer (30 mM NaPi, pH~6.5) and concentrated to the desired concentration in an Amicon concentration tube (3 kDa MWCO) (Merck). The PRR2 peptide was dissolved in $D_20$ to a final concentration 14-fold higher than the SH3 domain and combined with the SH3 sample, affording SH3/PRR2 complex in 7% $^2H_2O$ solution to which $NaN_3$ (0.02% v/v) was added. Final sample concentrations were 0.7-1.0 mM at a 1:1 molar ratio SH3:PRR2. For quantitative titrations, purchased peptides were dissolved in 100-300 μl NMR sample buffer, and samples at varying (SH3:PRR2 1:0-1:6, SH3 concentration constant at 0.1 mM) ratios were prepared. Fittings were performed with 5-6 measured points.

NMR Spectroscopy

NMR measurements were conducted on a DRX700 Bruker spectrometer (Bruker BioSpin GmbH, Rheinstetten, Germany) with a cryogenic triple-resonance TCI probe head equipped with z-axis pulsed-field gradients at 16.4 T and 296-298 K. External calibration was performed with DSS dissolved in the same buffer as for the experiments. Acquisition parameters for 2D TOCSY, NOESY and COSY homonuclear experiments, 2D HSQC experiments, the triple resonance HNCACB experiment, and 3D filtered-edited NOESY experiments are detailed below. For two-dimensional homonuclear experiments (COSY, TOCSY, and NOESY) 2048 complex points were acquired in the direct dimension ($^1H$) (acquisition time: 208.9 ms) and 280-480 complex points in the indirect dimension ($^1H$) (acquisition times: 40-57.1 ms), with mixing times of 150 ms (TOCSY) or 200-300 ms (NOESY). Typical experiment times were 3-36 h. Conditions for filtered-edited NOESY were 1024 complex points in the direct dimension ($^1H$), 96-97 complex points in the indirect $^1H$ dimension, and 25 complex points in the $^{13}C$ dimension, affording acquisition times of 104.4 ms, 4.2-5.3 ms, and 17.1 ms, respectively, and a mixing time of 200-400 ms throughout 59-66 h. $^{15}N$, $^1H$-HSQC spectra were acquired at 1024 complex points in the $^{1}H$ dimension and 188 complex points in the $^{15}N$ dimension (acquisition times: 91.8 ms and 88.3 ms, respectively). The HNCACB experiment (90 h) was acquired at 1024 complex points in the direct $^{1}H$ dimension and 40 (52) complex points in the indirect $^{15}N$ ($^{13}C$) dimension, affording acquisition times of 104.4, 16.6, and 4.9 ms, respectively. The aromatic-TROSY $^{13}C$, $^{1}H$ correlation spectrum (1.5 h) was acquired with 1024 complex points in the direct $^{1}H$ dimension and 100 complex points in the indirect $^{13}C$ dimension. Assignment of the unbound SH3 domain was assisted by BMRB entry 10240. Chemical shift perturbation values representing a normalized Euclidean distance $\Delta\delta$ were calculated as $((\Delta_H)^2+(0.14*\Delta_N)_2)^{1/2}$, where $\Delta_H$ and $\Delta_N$ are the shifts in the hydrogen and nitrogen dimensions, respectively.

NMR Affinity Determination

The $^{1}H$, $^{15}N$-HSQC spectrum of a 0.2 mM sample of the SH3 domain was acquired at 0:1 (black), 0.5:1, 1:1, 2:1 and 4:1 (light green) mol:mol PRR2:SH3 and 0:1 (black), 0.75:1, 1.5:1, 3:1 and 6:1 (light green) mol:mol PRR3:SH3. Peptides were unlabeled in all cases. Isotherms were fitted to the equation $$\alpha = \frac{n + 1 + \frac{K_D}{C} - \sqrt{\left(n + 1 + \frac{K_D}{C}\right)^2 - 4n}}{2}$$

where $\alpha$ is the fraction of bound SH3, n is the mol:mol equivalent ratio, $K_D$ the dissociation constant and C the SH3 domain concentration (0.2 mM) maintained constant by preparing multiple samples with an identical amount of SH3 stock solution. $\alpha$ was calculated as $CSP/CSP_{max}$. Both $K_D$ and $CSP_{max}$ were treated as fitted parameters based on multiple measurements of CSP at various n values.

Structure Calculation

NOE crosspeaks were ranked by intensity and binned into 4 groups corresponding to distances of 2.7, 3.3, 4.0-4.5 and 5.0-5.5 Å. Dihedral angle constraints were derived from the TALOS+ server [14] from SH3 domain HA, HN, CA and CB chemical shifts. Initial structures were calculated using distance and dihedral angle constraints by simulated annealing and torsional angle dynamics as applied in the program CNS [15]. Final structures were calculated with CNS using distance, dihedral, and H-bond constraints in addition to two electrostatic constraints, SH3(E506)-PRR2(R719) and SH3 (D522)-PRR2(K721) suggested by the NOESY data and derived from characteristic salt-bridge patterns in SH3 complexes. Stereochemical quality of the ensemble of final structures was evaluated using with VADAR 1.8 and PROCHECK. For the final ensemble of 20 structures, 100 structures were generated, and structures with lowest-energy and highest stereochemical quality were chosen by analysis with PROCHECK. Final coordinates were deposited at the Protein Data Bank under accession code 7PLL.

Statistical Analysis

Statistical analysis was performed using GraphPad Prism 8.0. For XTT, cortactin phosphorylation, and barbed end assays, statistical significance was calculated using two-way ANOVA followed by Bonferroni post-hoc test. For all other cellular and in vivo assays, one-way ANOVA followed by Tukey's post-hoc test was used. For patient database analysis, statistical significance was calculated using log-rank and Student's t-test implemented in MATLAB. Values were considered statistically significant if the $P<0.05$. For all figures, *, $P<0.05$; , $P<0.01$; *, $P<0.001$. Error bars represent standard errors of the mean (SEM).

Figure 1B:
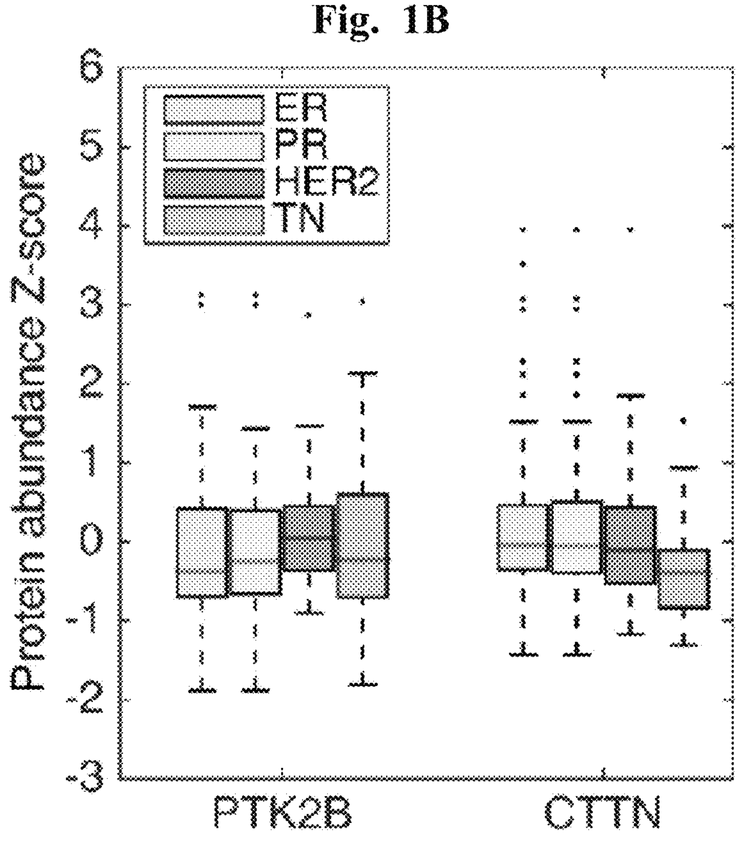
Figure 1C:
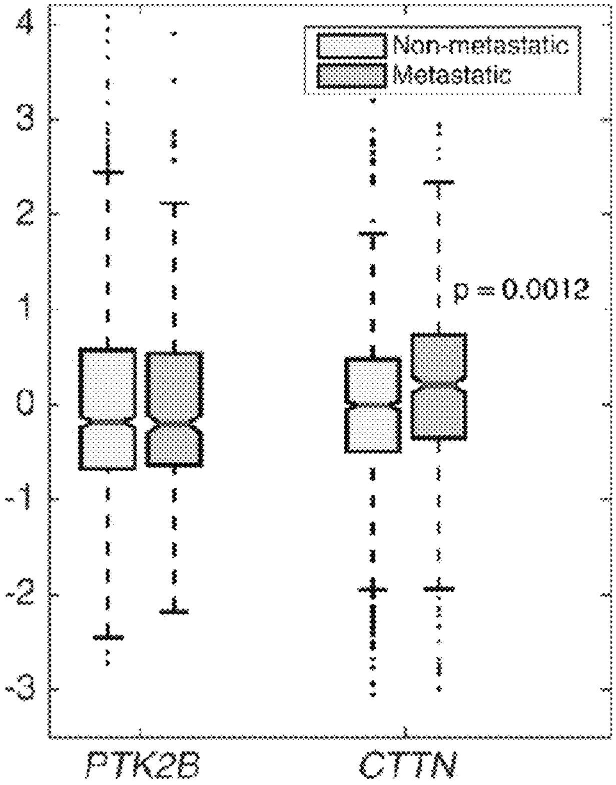
Figure 1D:
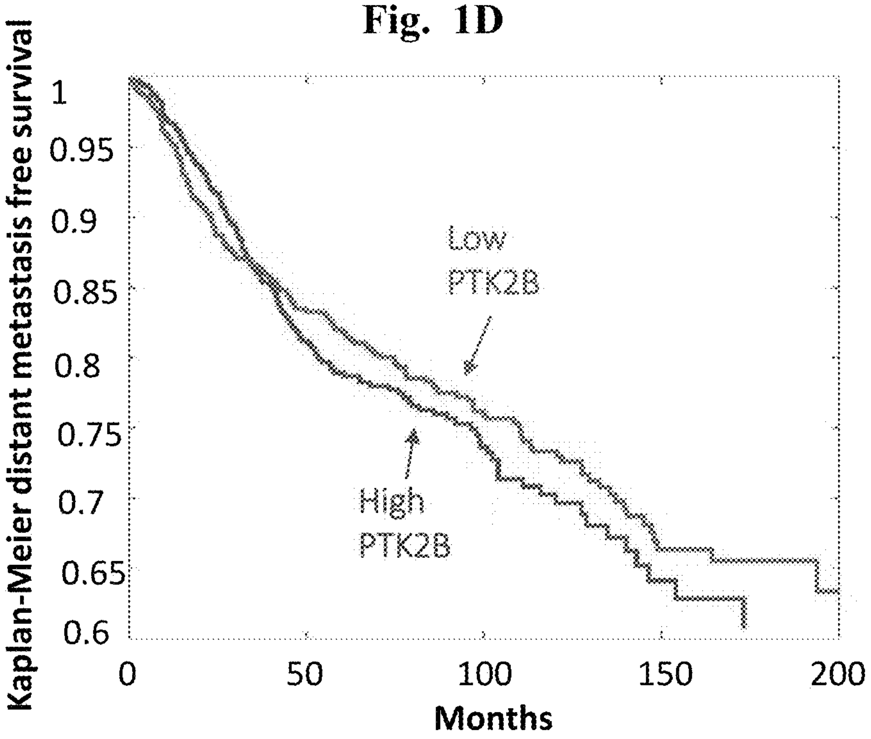
Figure 1E:
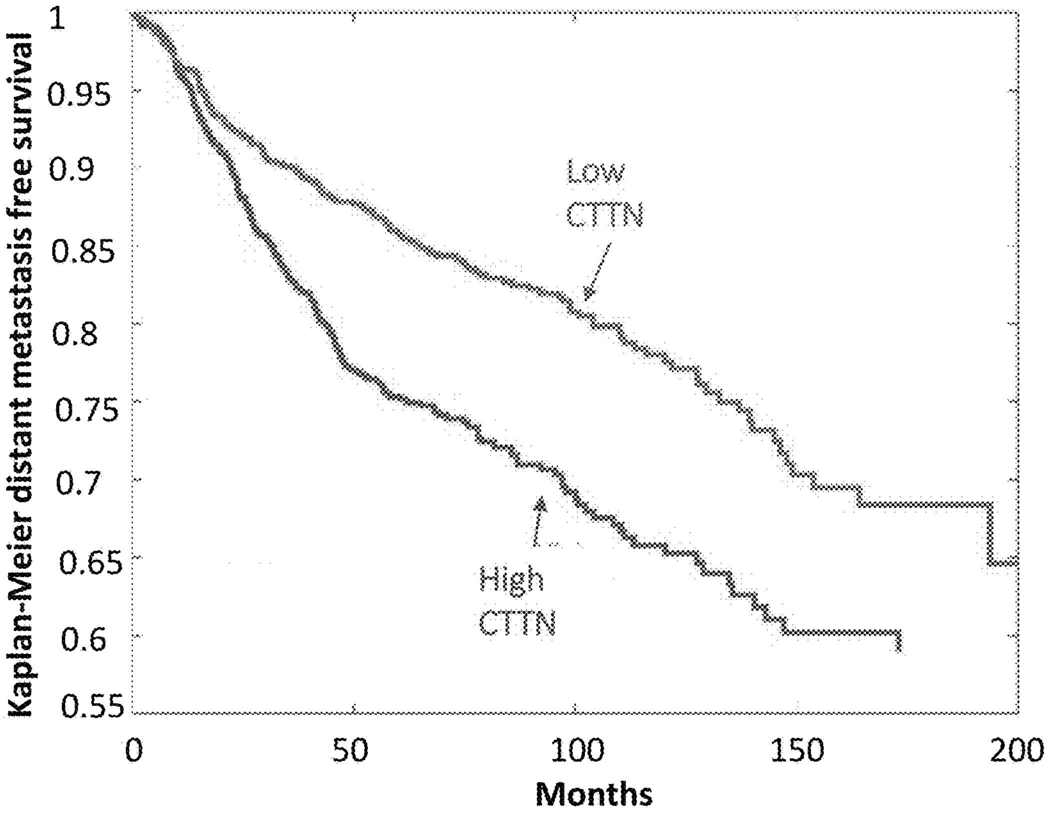
Figure 1F:
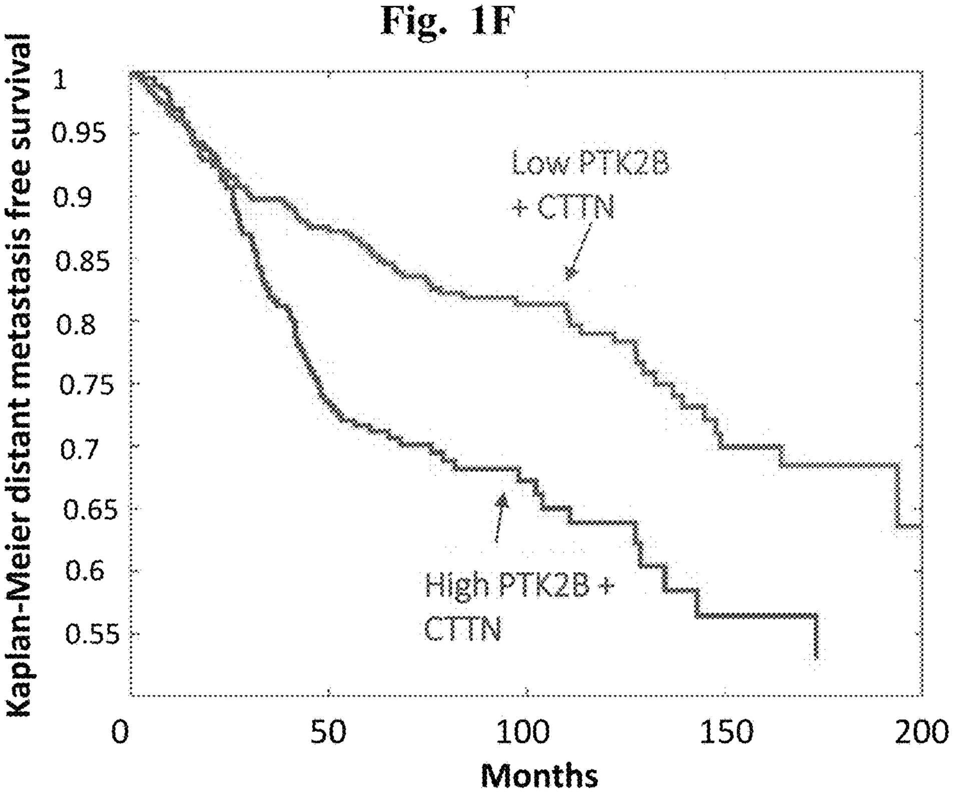

Example 1: Increased Expression of Pyk2 and Cortactin is Associated with Breast Cancer Metastasis and Poor Patient Prognosis The inventors have previously shown that the Pyk2/cortactin interaction is critical for invadopodia-mediated breast tumor cell invasiveness. To study this further, DNA, RNA, and protein expression data of breast cancer tissues from the cancer genome atlas (TCGA) was integrated and stratified by hormone- and HER2-receptor status. A comparison of copy number alterations (CNA), mRNA expression, and protein expression demonstrated similar distribution among all hormone- and HER2-receptor statuses (FIGS. 1A-1C), suggesting that Pyk2 and cortactin expression profile is not unique to any of the four primary molecular subtypes in breast cancer. To assess the involvement of Pyk2 and cortactin in metastatic dissemination, microarray expression levels of 1,650 breast cancer samples were analysed. The survival analysis showed significant association between poor distant metastasis free survival (DMFS) and high mRNA levels of CTTN (HR 1.56, 95% CI 1.29-1.93; $p<0.001$) but not with PTK2B (the Pyk2 encoding gene) (HR 1.06, 95% CI 0.86-1.30; $p=0.62$) (FIGS. 1D-1E). However, the combined effect of PTK2B and CTTN overexpression considerably reduced DMFS estimates (HR 1.72, 95% CI 1.29-2.30;$p<0.001$) with a synergy index (SI) of 1.13 (FIG. 1F), suggesting that Pyk2 and cortactin act synergistically to promote breast cancer metastasis, and that inhibition of their interaction may blocks this process.

Figure 2A:
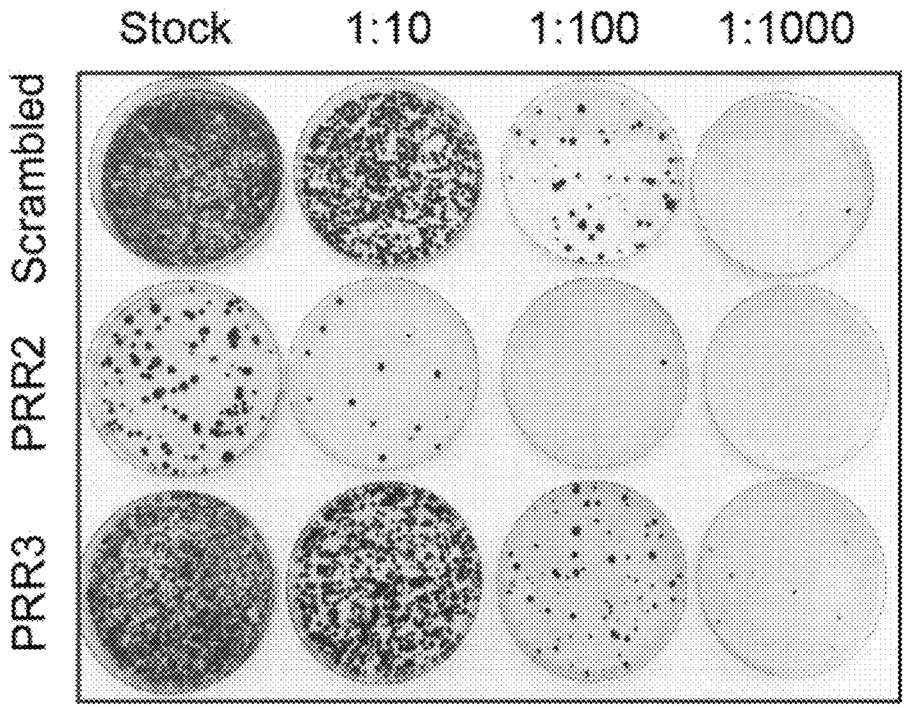
FIGS. 2A-2G show that a cell-permeable peptide derived from the second proline-rich region of Pyk2 blocks spontaneous lung metastasis in an immune-competent xenograft mouse model. 4T 1 cells were injected into the mammary fat pad of 8-week-old BALB/c female mice and allowed to grow for 12 days until the tumor reached the size of 100 $mm^3$. On day 13 following injection, mice were treated by intraperitoneal injection with 10 mg/kg of scrambled control, Pyk2-PRR2, or Pyk2-PRR3 once a day for eight days. Lungs were dissected at the end of the experiment, dissociated, and plated in different dilutions in a medium containing 6-thioguanine for 14 days. On day 14, 6-thioguanine-resistant colonies were stained with crystal violet, and colonies were counted.
Figure 2B:
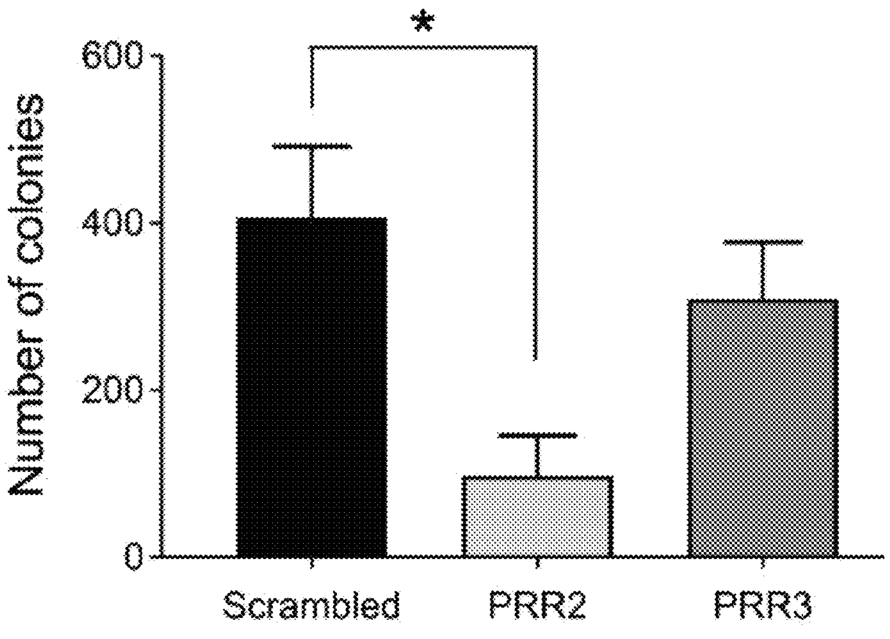

Example 2: A Peptide Derived from the Second Proline-Rich Region of Pyk2 Blocks Spontaneous Lung Metastasis in an Immune-Competent Xenograft Mouse Model Pyk2 peptides derived from the second (Pyk2-PRR2, SEQ ID NO: 1) or third (Pyk2-PRR3, SEQ ID NO: 2) proline-rich regions and a control scrambled peptide (SEQ ID NO: 4) were synthesized and fused to an HIV-TAT sequence to increase their permeability into cells. To examine their effect on breast cancer metastasis in mice, the highly tumorigenic mouse 4T1 cell line was used. This cell line efficiently forms mammary tumors upon injection into the mammary fat pad of syngeneic immune-competent BALB/c mice and spontaneously metastasizes to multiple distant sites in a pattern similar to that of human breast cancer. Tumor-bearing mice were treated with the peptides by intraperitoneal injection for 8 days, followed by careful examination and quantification of lung metastases at the end of the treatment. As demonstrated in FIGS. 2A-2B, mice treated with Pyk2-PRR2 exhibited significantly fewer lung metastases than scrambled peptide- or Pyk2-PRR3-treated mice bearing equal-sized tumors.

Figure 2C:
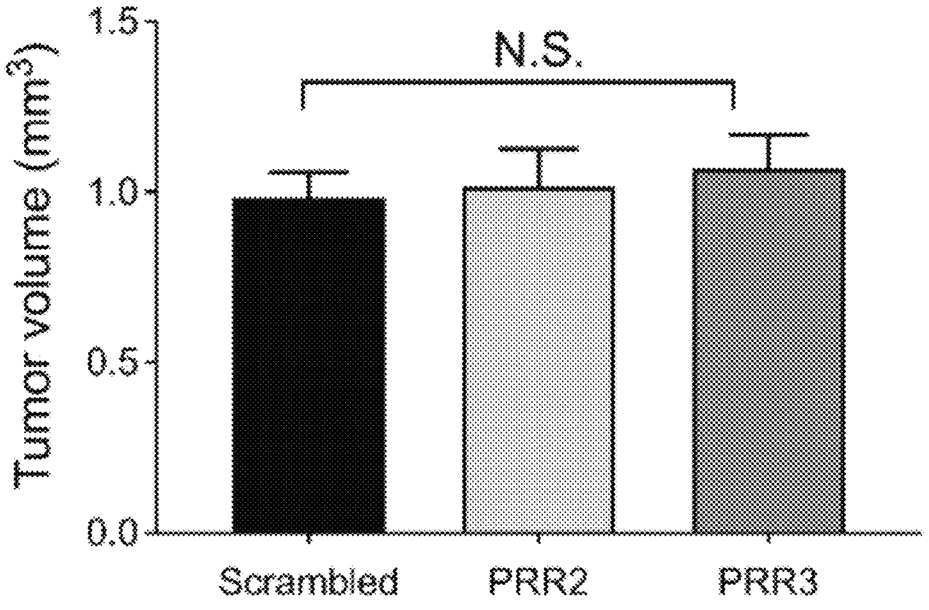
Figure 2D:
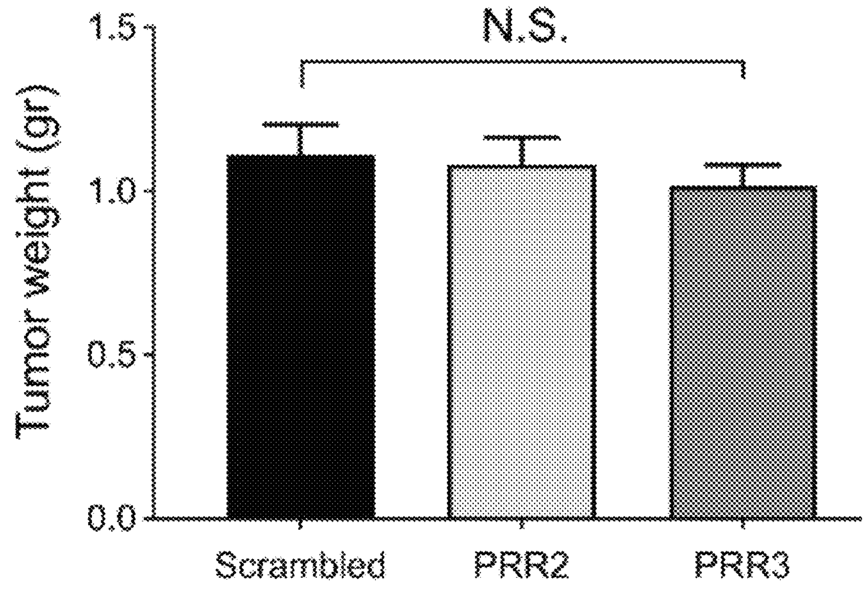
Figure 2E:
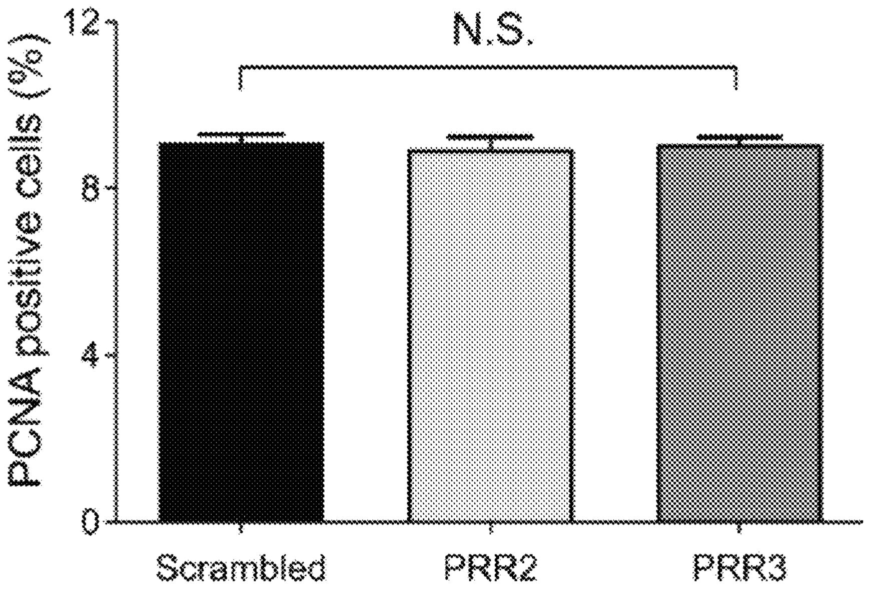
Figure 2F:
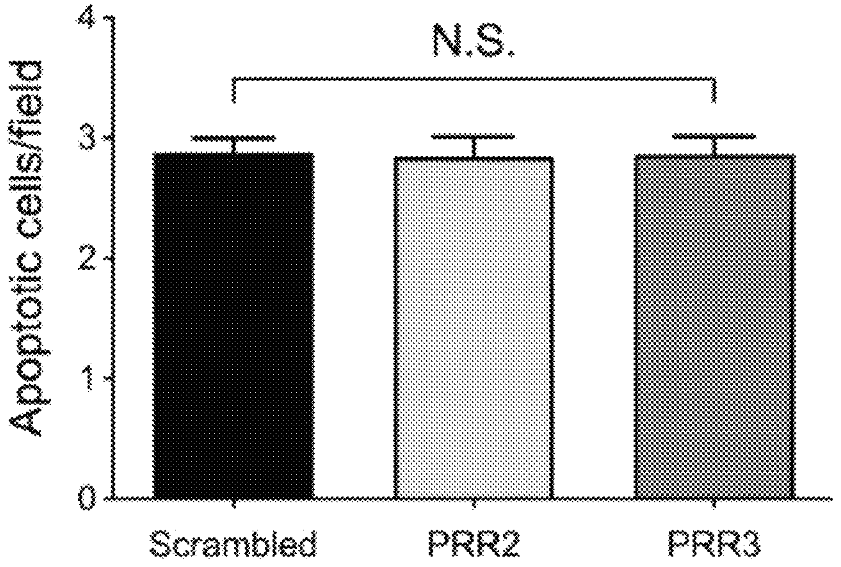
Figure 2G:
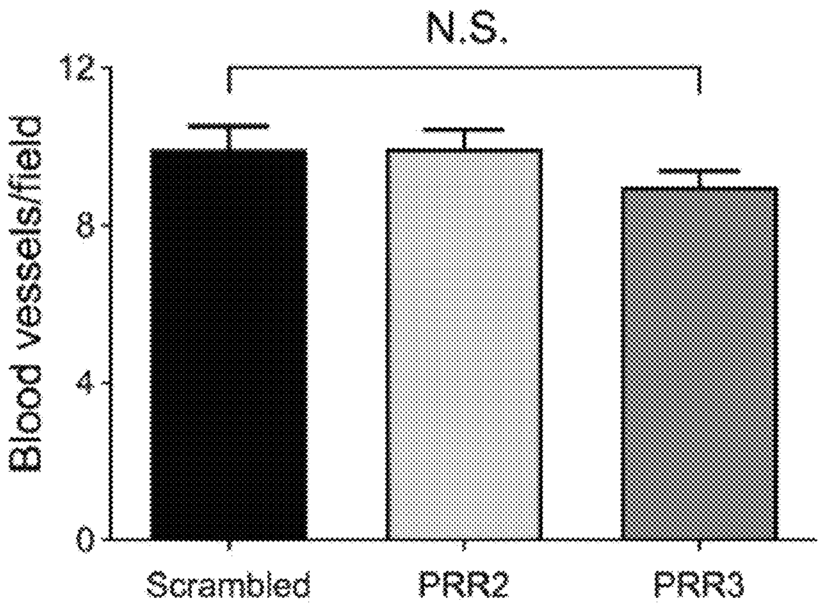

To investigate these further, primary tumors were isolated and examined at the end of the treatment. As demonstrated in FIGS. 2C-2D, no significant differences in tumor size or weight were observed in mice treated with Pyk2-PRR peptides or the scrambled control. Accordingly, and as observed by immunofluorescent histological labeling, no significant differences were observed in proliferation, apoptosis, or angiogenesis in tumors from the different groups (FIGS. 2E-2G). Collectively, these data suggest that while none of the peptides suppressed primary tumor growth, the Pyk2-

PRR2 peptide, but not Pyk2-PRR3 peptide, can suppress in vivo breast tumor metastasis in immune-competent mice bearing equal sized tumors.

Example 3: Pyk2-PRR2 Suppresses MMP-Dependent 3D Invasiveness of Breast Tumor Cells Metastatic dissemination is initiated by the invasion of tumor cells through the tumor basement membrane and extracellular matrix (ECM). To study the effect of Pyk2 peptides on tumor cell invasiveness, the MDA-MB-231 was used, a highly invasive, triple-negative basal-like human breast adenocarcinoma cell line that forms functional invadopodia in culture.

Peptide permeability into MDA-MB-231 cells was validated using an immunofluorescence assay, showing all peptides penetrated the cells and were stable at least 24 h following incubation. An XTT assay on cells incubated with 0.1, 1, 5, and 10 M concentrations of peptides showed that the three lower concentrations did not affect cell viability and were therefore used in all further cellular studies (data not shown).

Figure 3A:
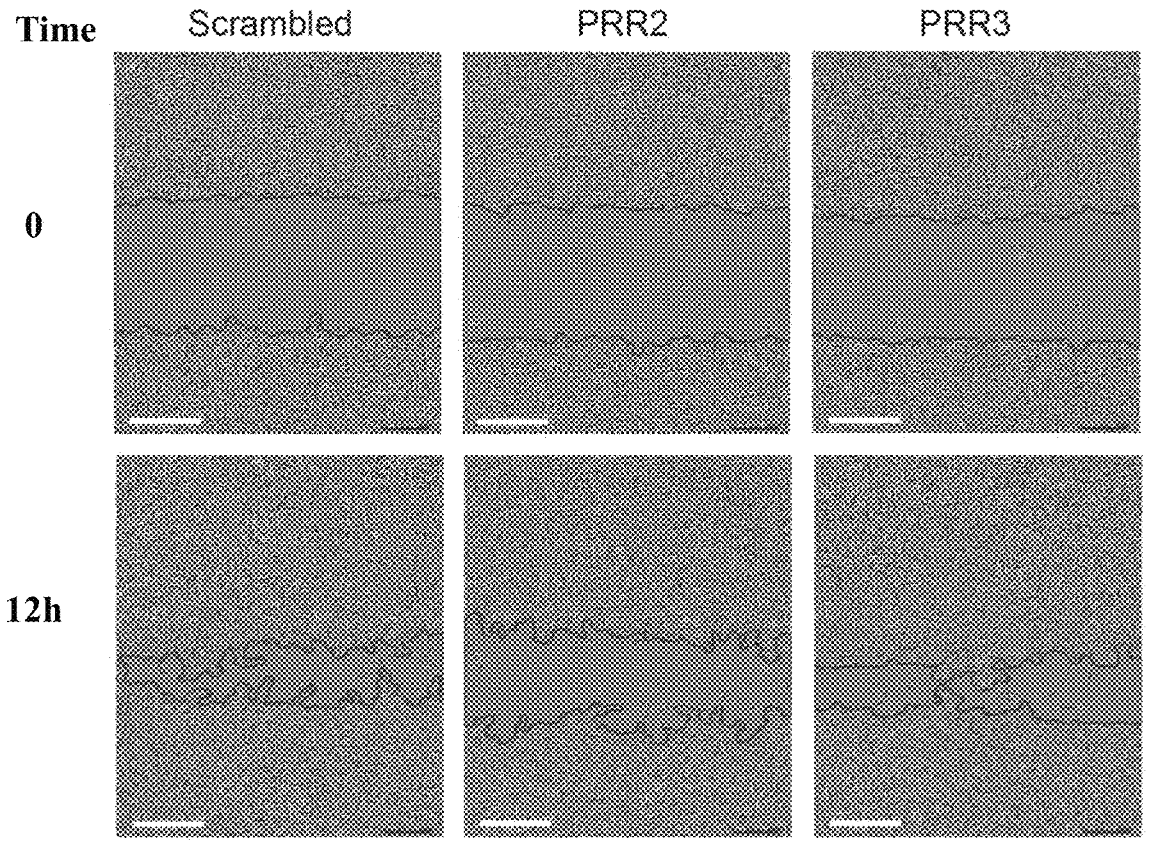
FIGS. 3A-3G show that Pyk2-PRR2 suppresses MMP-dependent 3D invasiveness of breast tumor cells.
Figure 3B:
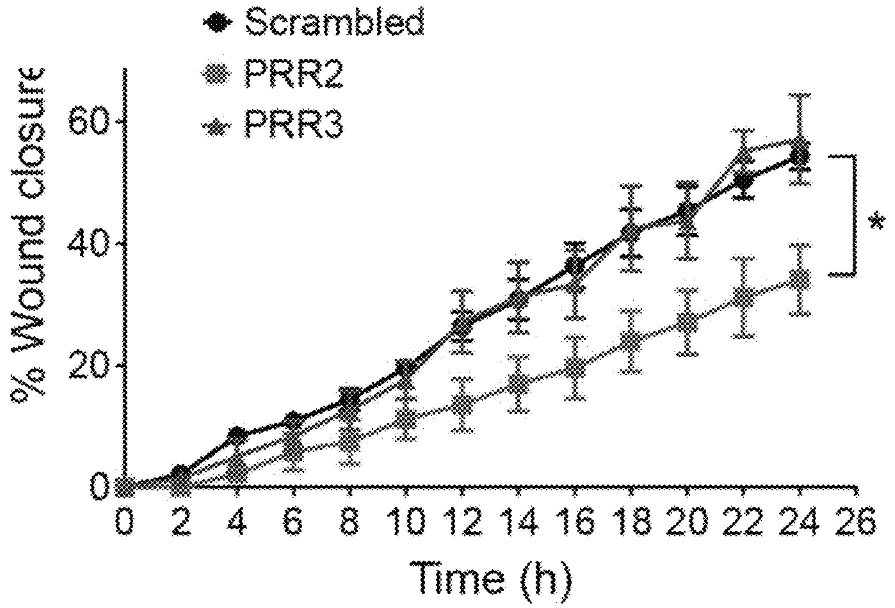
Figure 3C:
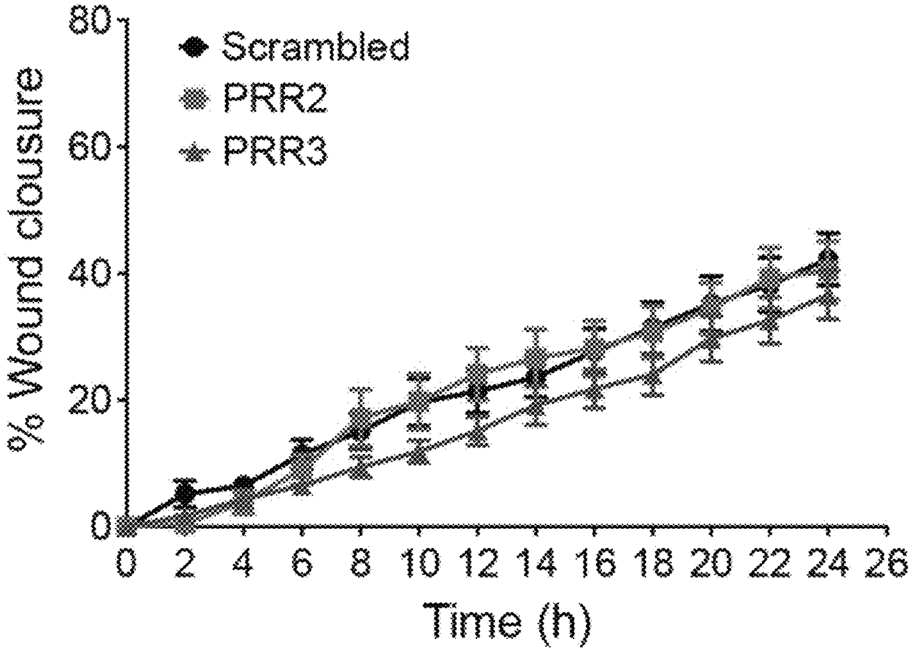
Figure 3D:
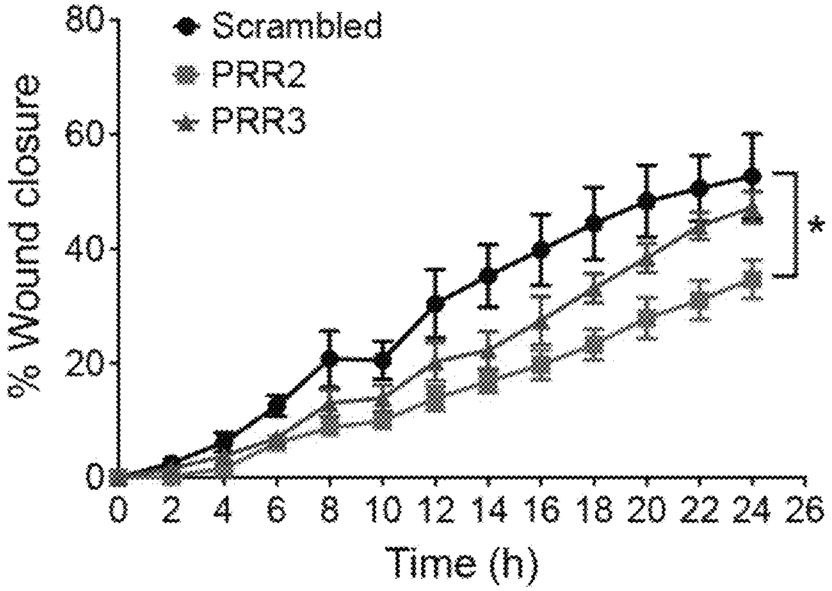
Figure 3E:
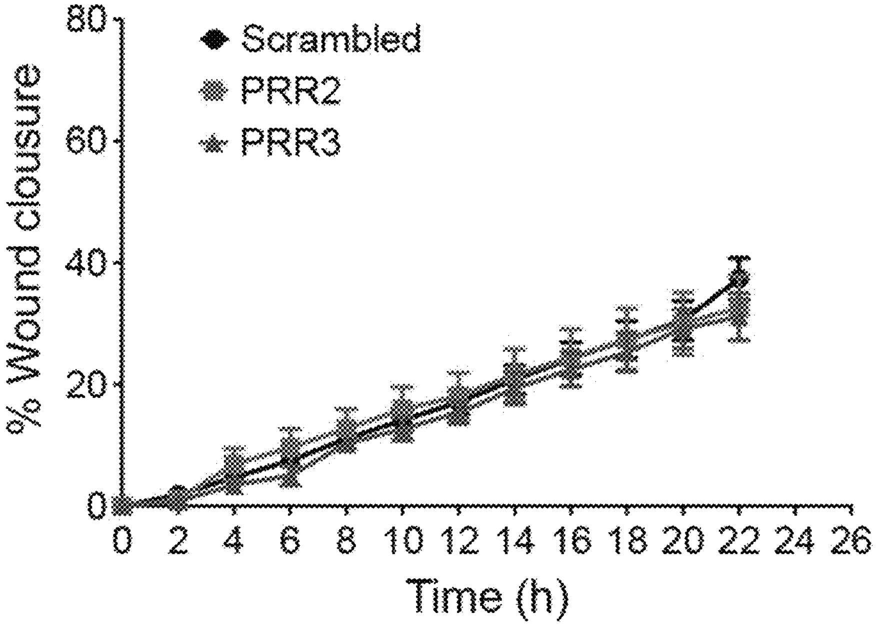
Figure 3F:
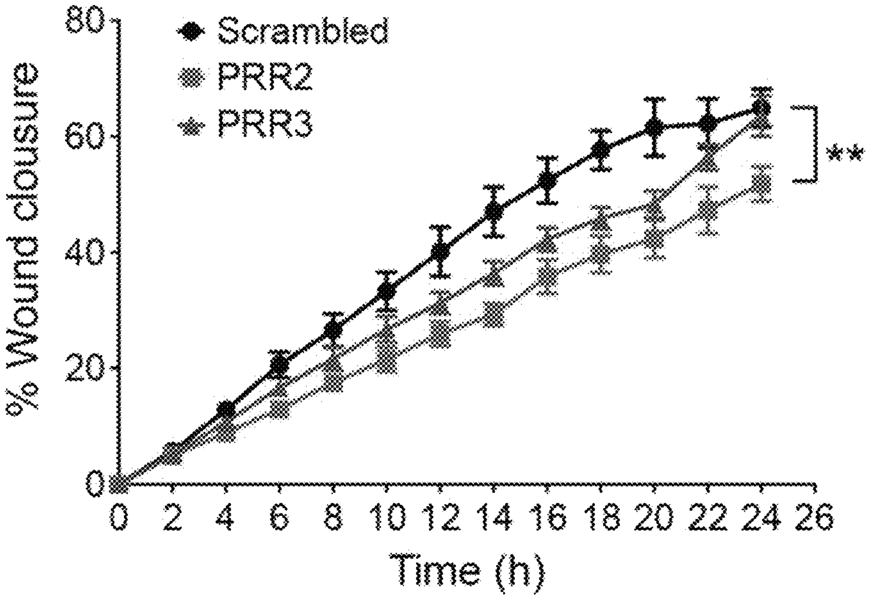
Figure 3G:
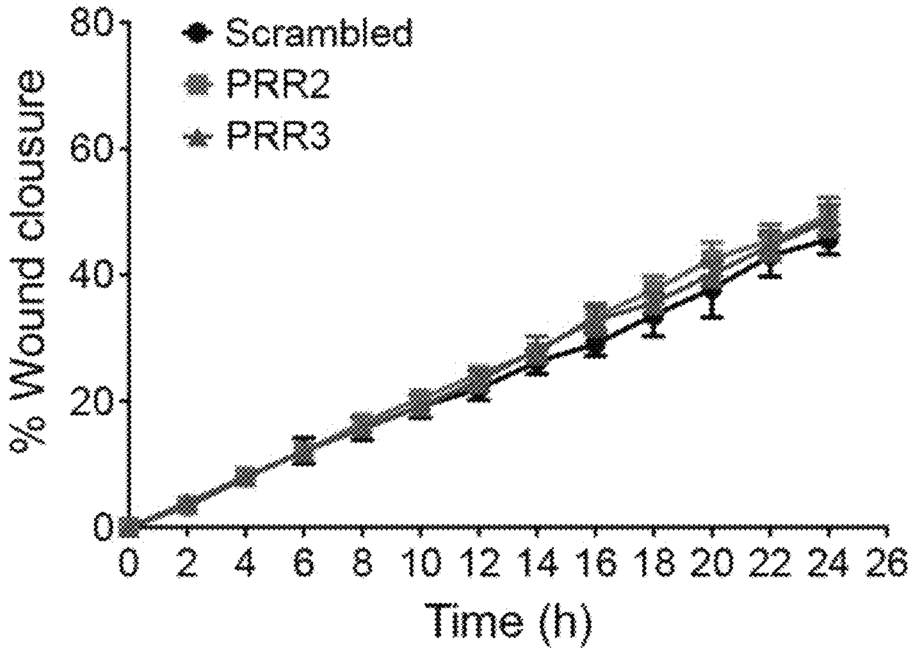

The ability of the three peptides to inhibit the invasion of breast cancer cells embedded in a three-dimensional (3D) Matrigel matrix towards a scratch wound was tested over 24 hours. As demonstrated in FIG. 3A, cells treated with the Pyk2-PRR2 peptide, but not with the Pyk2-PRR3 or control peptides, showed significantly reduced ability to close the gap by invading towards the wound. Significantly, ECM invasion was always fully inhibited by MMP inhibitor GM6001 (FIGS. 3B-3G), confirming that this invasion is MMP-mediated and that the Pyk2-PRR2 peptide inhibits MMP-dependent tumor cell invasiveness.

Further evidence of the Pyk2-PRR2 effect upon tumor cell invasiveness was provided by a 2D random migration assay. Invasiveness is controlled by coordinating MMP-dependent invadopodia-mediated invasion and focal adhesion-mediated motility, and the inventors have previously shown that Pyk2 localizes to these regions and that knockdown of Pyk2 inhibits both MMP-dependent invasion and two-dimensional (2D) motility. Following accumulated and Euclidean distances as well as velocity over 12 hours, cells treated with Pyk2-PRR2 at all concentrations and with Pyk2-PRR3 at the highest concentration showed reduced 2D motility over an ECM substrate compared to the control peptide (data not shown). Thus, Pyk2-PRR2, and to a lesser extent Pyk2-PRR3, regulate 2D motility and inhibit tumor cell invasiveness.

Example 4: The Pyk2-PRR2 Peptide Inhibits the Interaction Between Pyk2 and Cortactin in Invadopodia and Consequent Invadopodium Maturation and Function in Breast Tumor Cells Breast cancer metastasis has previously been correlated in vivo with invadopodia maturation and function, and in mouse models and human patients with invadopodia assembly and function.

Figure 4A:
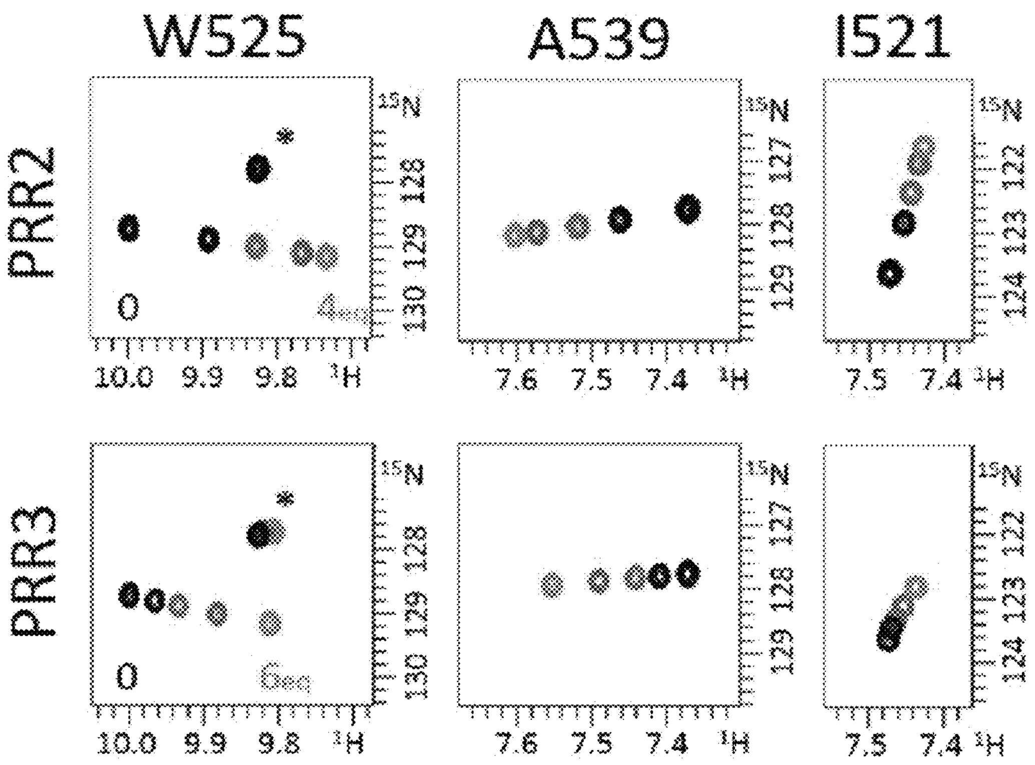
FIGS. 4A-4F show that Pyk2-PRR2 peptide inhibits Pyk2-cortactin interactions in invadopodia and consequent invadopodium maturation and function in breast tumor cells.
Figure 4B:
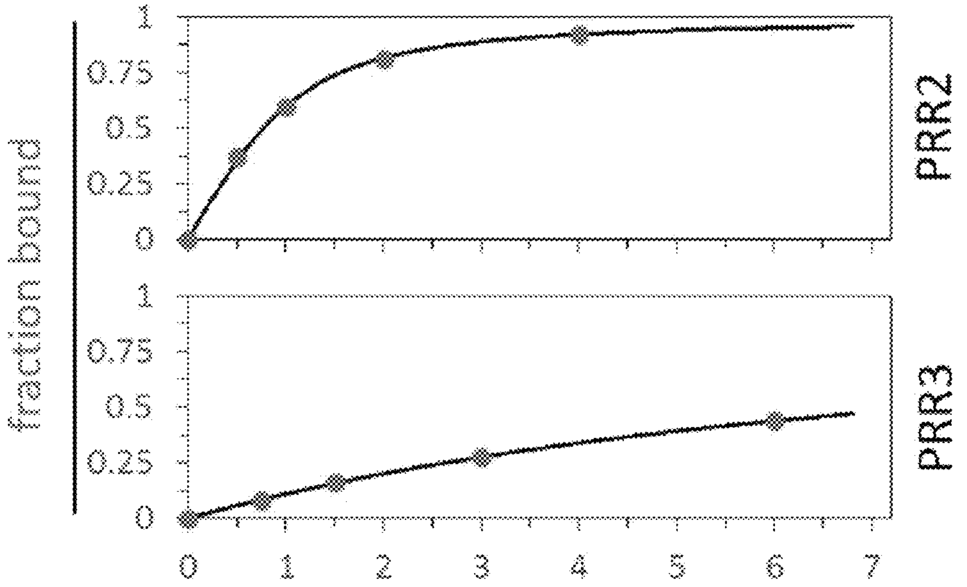

Binding of Pyk2-PRR peptides to purified cortactin-SH3 was determined by following ligand-induced chemical shift changes along the course of a titration isotherm. Pyk2-PRR2 (SEQ ID NO: 1) and Pyk2-PRR3 (SEQ ID NO: 2) ligands exhibited affinities of $K_D$=40±5 and $K_D$=650±10 μM, respectively, and the Pyk2-PRR2 derivatives HAIYPRHTAFQEPPPKPSRPKYRPPP-$NH_2$ (SEQ ID NO: 7+C-term cap), Ac-TAFQEPPPKPSRPKYRPPPHRPYIAH (SEQ ID NO: 8+N-term cap), and Ac-T*A*F*Q*EPPPKPSRPKYR*P*P*P*-$NH_2$ (SEQ ID NO: 9+N- and C-term caps) wherein * denotes d-amino acid exhibited affinities of $K_D$=8±5, $K_D$=2±1 and $K_D$=15±2, while a scrambled control peptide did not display significant affinity to the SH3 domain ($K_D$>1 mM) (FIGS. 4A-4B).

Figure 4C:
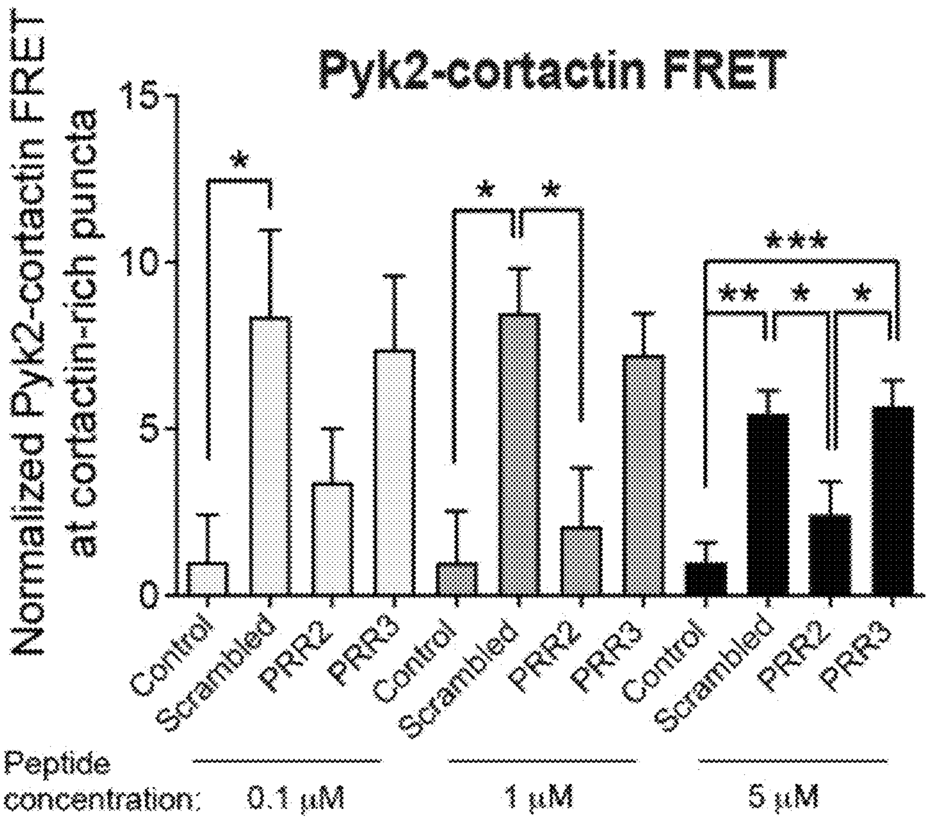

Largest Pyk2-PRR2-induced changes were observed for residues I521, A539 and the W525 of the cortactin indole cross-peak, consistent with a canonical binding mode. Thus, the Pyk2-PRR2 peptide binds to cortactin SH3 in vitro with a significantly (16-fold) higher affinity than Pyk2-PRR3. The ability of Pyk2-PRR2 to block the access of Pyk2 to cortactin in invadopodia in Forster resonance energy transfer (FRET) acceptor photobleaching experiments was also measured. These demonstrated that the Pyk2-PRR2, but not Pyk2-PRR3 or a scrambled peptide, significantly inhibited the interaction between Pyk2 and cortactin in invadopodia (FIG. 4C).

Figure 4D:
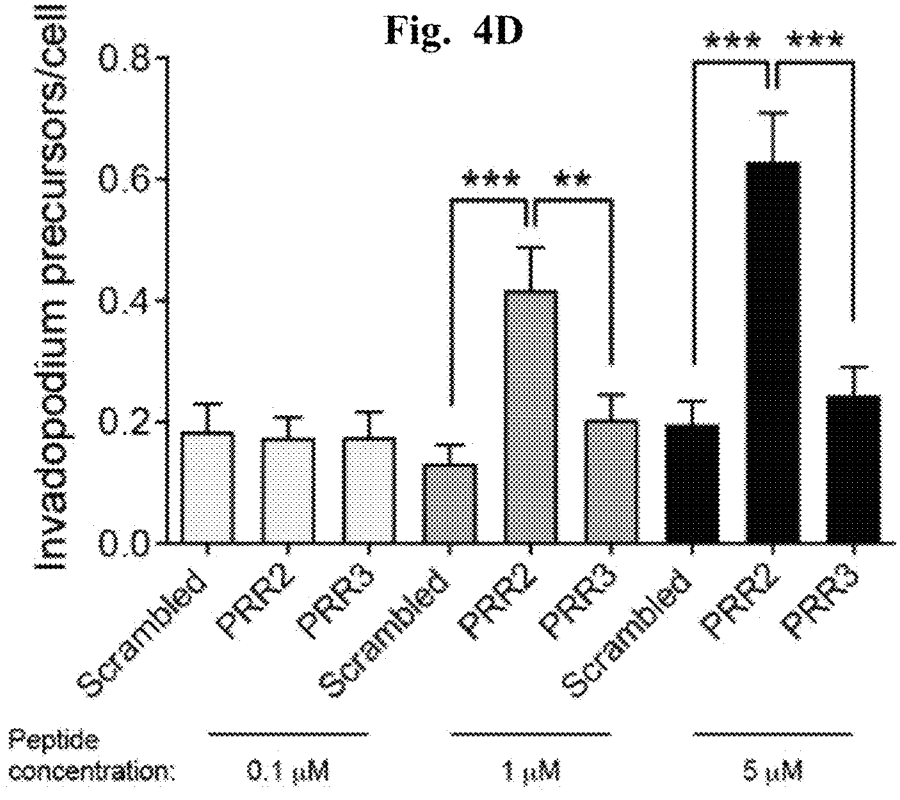
Figure 4E:
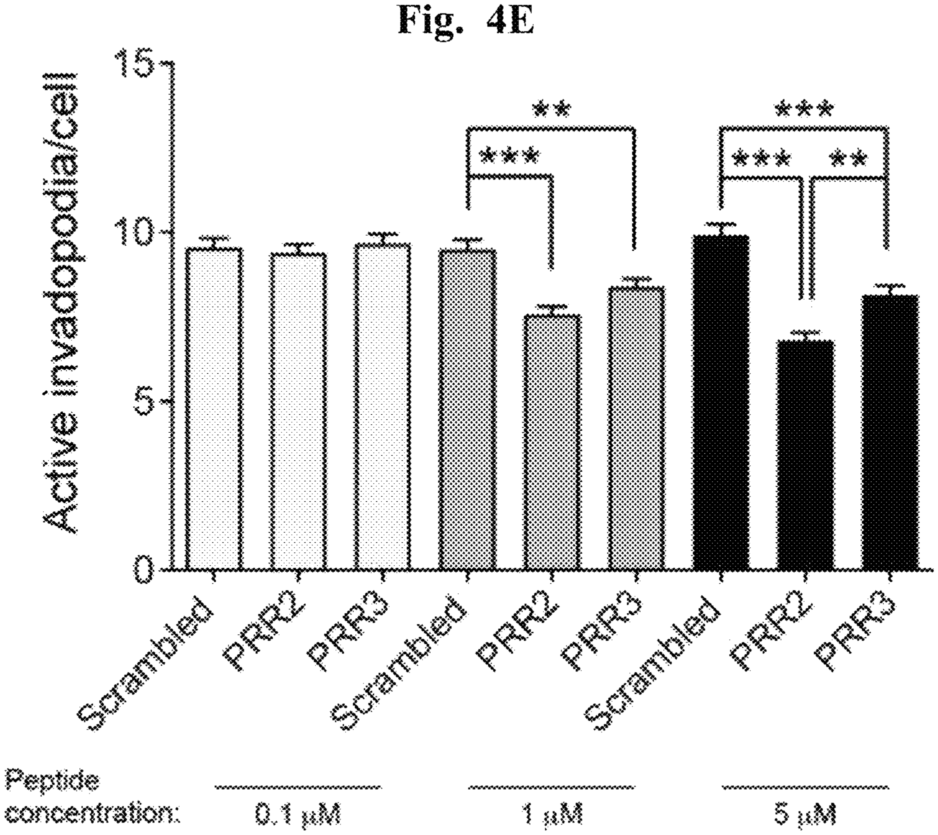

To examine whether Pyk2-PRR2 regulates the initial assembly of invadopodium precursors, MDA-MB-231 cells were treated with Pyk2-PRR2, Pyk2-PRR3, or scrambled control peptide, plated on fluorescently labeled gelatin matrix and labeled for Tks5 and cortactin as invadopodium precursor markers. The significant increase in immature invadopodium precursors, along with a significant decrease in mature, matrix-degrading invadopodia observed in Pyk2-PRR2-treated cells implied that this peptide blocks the maturation and activation of pre-assembled invadopodium precursors in breast tumor cells (FIGS. 4D-4E). The minor effect of Pyk2-PRR3 at higher peptide concentrations in both 2D motility and in invadopodia formation and maturation is consistent with its weaker binding affinity to cortactin-SH3 and lower similarity to the cortactin consensus motif.

Figure 4F:
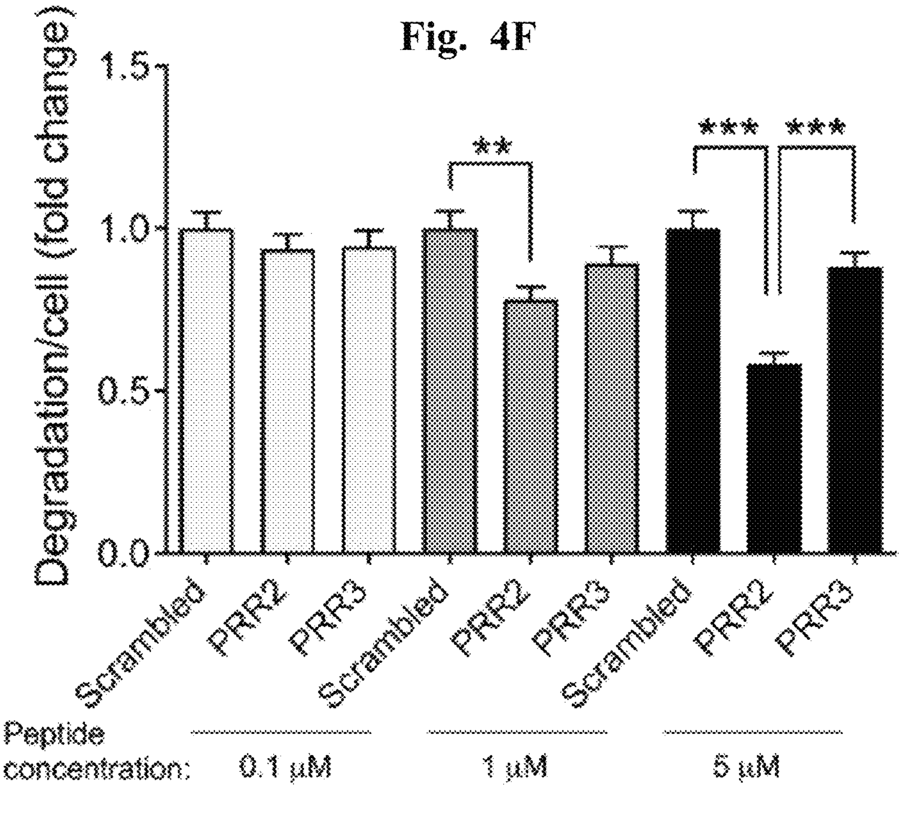

At the final maturation stage invadopodia locally degrade the ECM by secretion and activation of MMPs, allowing invasive cancer cells to leave the primary tumor and penetrate blood vessels. Breast tumor cells were plated on fluorescent fibronectin/gelatin matrix and allowed to degrade the matrix for 24 h in the presence of increasing concentrations of control, Pyk2-PRR2, or Pyk2-PRR3 peptides. Quantification of the degradation area revealed a significant decrease in the ability of Pyk2-PRR2 treated cells to degrade the matrix in all concentrations tested (FIG. 4F). Taken together, these data suggest that the Pyk2-PRR2 peptide inhibits invadopodia maturation and activation and consequent MMP-dependent matrix degradation, which further supports our in vitro 3D invasion and our in vivo metastasis phenotypes.

Figure 5A:
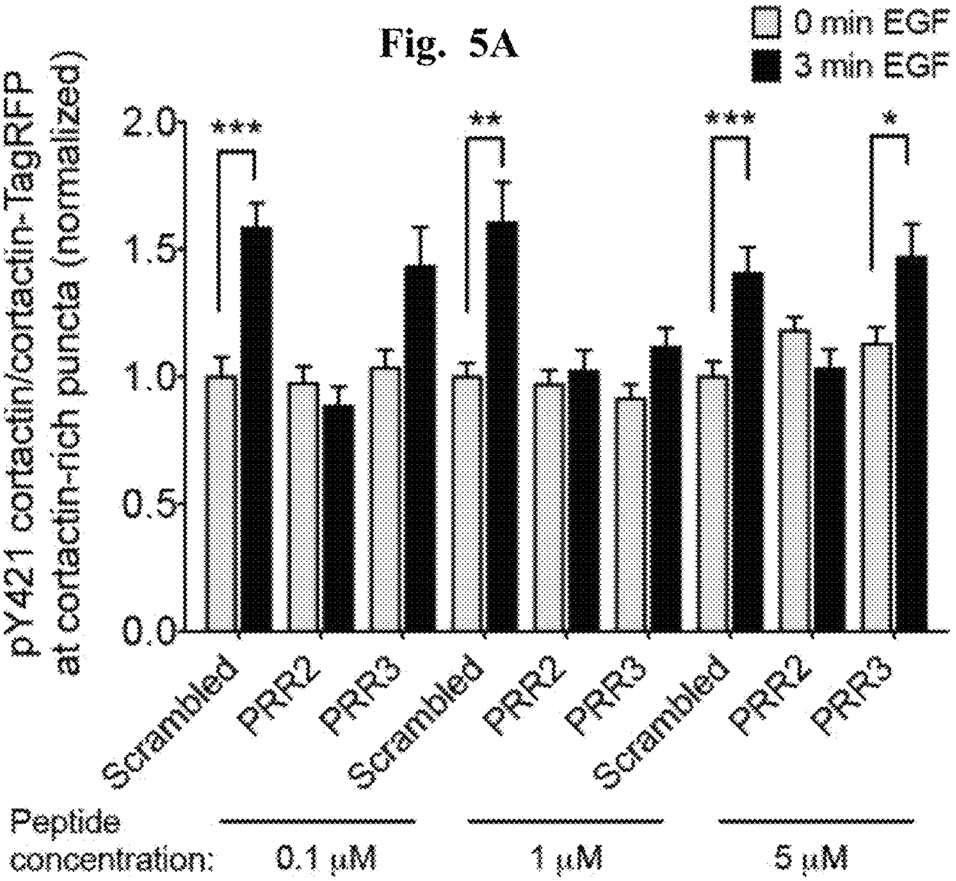
FIGS. 5A-5B show that Pyk2-PRR2 inhibits cortactin tyrosine phosphorylation and consequent barbed end formation in invadopodia.
Figure 5B:
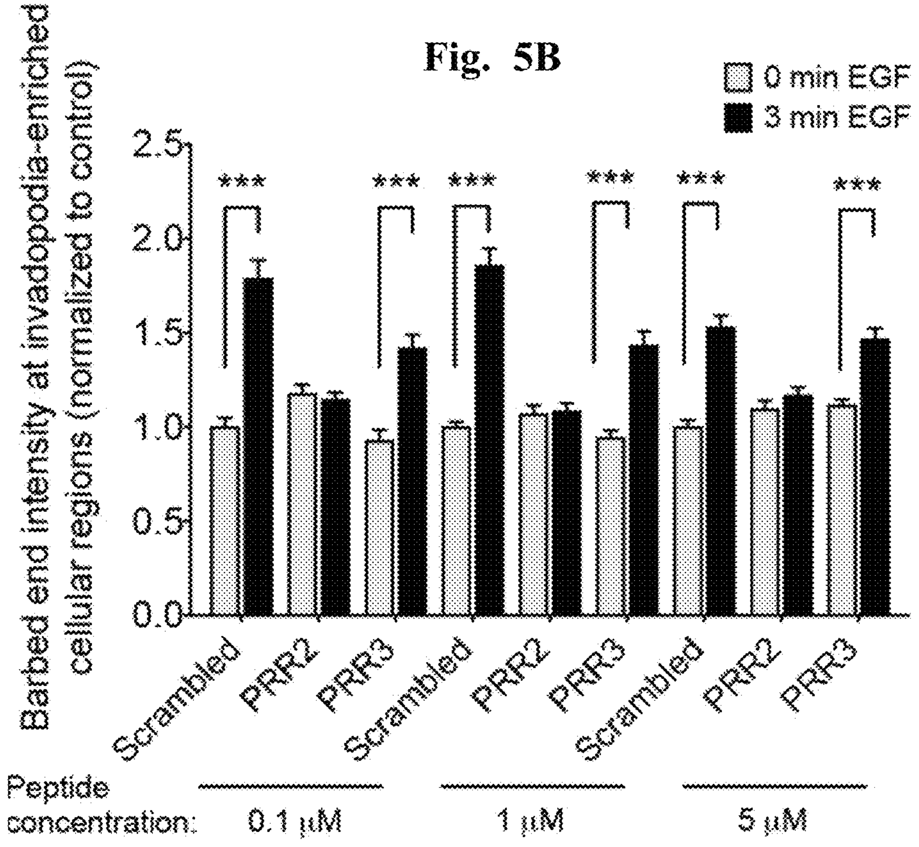

Example 5: Pyk2-PRR2 Inhibits Cortactin Tyrosine Phosphorylation and Consequent Barbed End Generation in Invadopodia of Breast Cancer Cells Tyrosine phosphorylation of invadopodial cortactin mediates invadopodia maturation and activation, and involves the Pyk2 kinase, both directly and indirectly via Src-mediated Arg activation. To see whether Pyk2-PRR peptides can inhibit this process in breast cancer cells, MDA-MB-231 cells stably expressing Tag-RFP-cortactin were treated with Pyk2-PRR or control peptides and further induced to form invadopodia by EGF. Cells were then fixed and labeled with phosphorylation-specific antibodies for cortactin tyrosine Y421. As demonstrated in FIG. 5A, phosphorylation was completely abolished in Pyk2-PRR2-treated cells at all concentrations, suggesting that Pyk2-PRR2 regulates the maturation and functional activation of invadopodia by inhibiting cortactin tyrosine phosphorylation. It is likely that this occurs by interrupting the binding of tyrosine kinases that normally phosphorylate cortactin, such as Pyk2 and Arg, to the SH3 domain of cortactin. To confirm these results, the effect of Pyk2-PRR2 on generation of free actin barbed ends, a known consequence of phosphorylation required for actin polymerization followed by pushing of the invadopodium membrane into the ECM and penetration of tumor cells through it, was also examined. Peptide-treated cells with EGF were stimulated to synchronize the generation of free actin barbed ends within invadopodia, then quantified the generation of free actin barbed ends specifically within these structures (FIG. 5B). Whereas EGF stimulation generated a 1.3-1.8-fold increase in barbed end intensity in control- and Pyk2-PRR3-treated tumor cells, treatment with the Pyk2-PRR2 peptide completely disrupted generation of free actin barbed ends at invadopodia at all concentrations. Thus, inhibition of phosphorylation appears to be involved in the mechanism of Pyk2-PRR2 peptide blocking of invadopodial maturation in breast tumor cells.

Example 6: The Structure of the Pyk2-PRR2/Cortactin-SH3 Complex Reveals an Extended Binding Interface With extensive evidence of the Pyk2-PRR2/cortactin-SH3 interaction and its potent role in regulating invadopodia-mediated metastasis, the complex was characterized at the molecular level to identify critical residues which contribute to the interaction affinity. The NMR-based SH3/PRR2 complex structure was determined using distance constraints established through homonuclear and filtered-edited heteronuclear NOESY experiments and dihedral angle constraints derived from analysis of chemical shifts (FIG. 6). The SH3 domain adopts the well-known double j-sheet fold with the long 02-strand stitching the two sheets and forming the SH3 hydrophobic core. However, the complex interface revealed a critical extension of the canonical binding surface, which has not been previously reported for cortactin complexes. While the canonical interface is formed by seven SH3 residues (Y497, Y499, E506, W525, P538, N540, Y541) which bind to the hallmark class II polyproline helix $^{713}$PPPKPSR$^{719}$, an additional interaction surface is formed between SH3 residues I521, D522, W525 and L536, and the Pyk2 extension $^{720}$PKY$^{722}$. In the canonical interface, the dipeptide motifs $^{713}$PPP$^{714}$ and $^{716}$KP$^{717}$ are inserted deepest in the two canonical SH3 binding grooves formed by residues Y497-Y541 and Y499-W525-P538-Y541, respectively. Concomitantly, residues P$^{717}$SRP$^{720}$ form a second 'arch' extending over the W525 indole ring, and residues $^{720}$PKY$^{722}$ contact the second binding surface (surface-II), including I521 and L536 (hydrophobic interaction with Y$^{722}$), W525 (interaction with P$^{720}$), and D522 (electrostatic interaction with K$^{721}$). These two SH3-PRR2 contacts contribute 844 and 424 Å$^2$, respectively, to the overall binding surface (1,268 A2) (FIG. 6A).

Three main features contribute to the affinity of this complex. First, a network of hydrogen bonds stabilizes the complex, including the P$^{714}$ CO with the Y541 sidechain hydroxyl, the P$^{715}$ CO with the N540 polar sidechain, and P717/S$^{718}$ CO groups with the W525 indole NH. In addition, stabilizing electrostatic contacts are found between R$^{719}$ and the acidic specificity pocket of SH3 residues D505/E506 and between K$^{721}$ and D522 in surface II (not shown). Second, the P$^{714}$/P$^{717}$/P$^{720}$ pyrrolidine rings adopt an orientation parallel to the SH3 groove-lining aromatic residues W525 and Y541, thus favoring C—H-π interactions between the electron-rich aromatic rings and the partial positive charge of polarized Cα-Hα and Cδ-Hδ bonds in prolines (not shown). Finally, close packing of hydrophobic surfaces is found for the three inserted proline residues and residue Y722 with the methyl groups of I521 and L536.

Figure 6B:
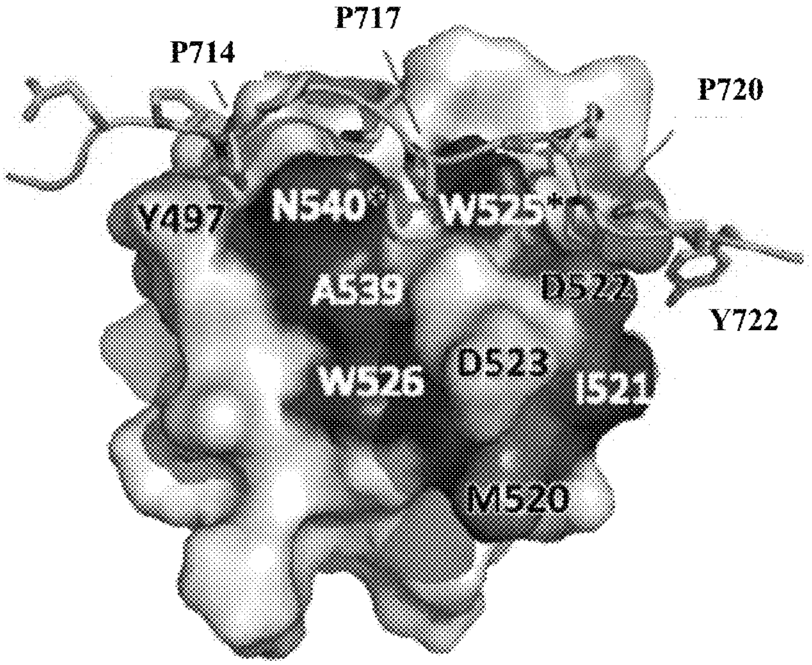
Figure 6C:
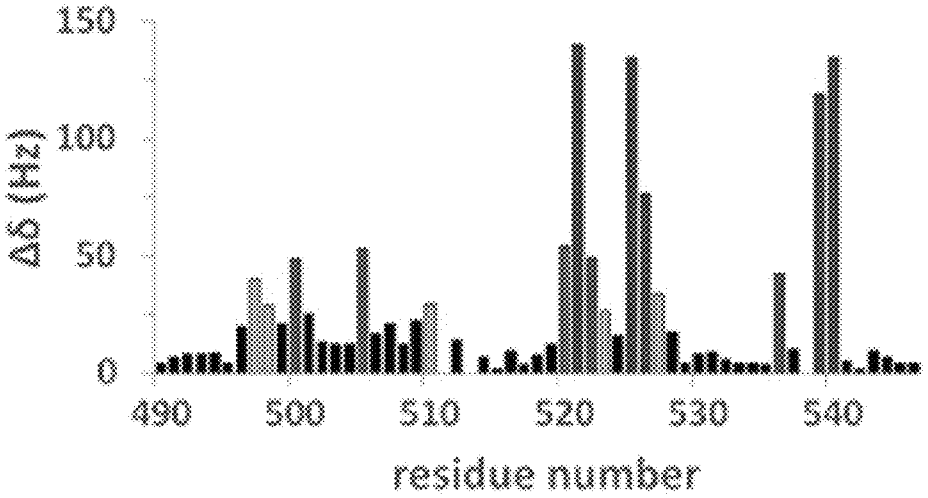
Figure 6D:
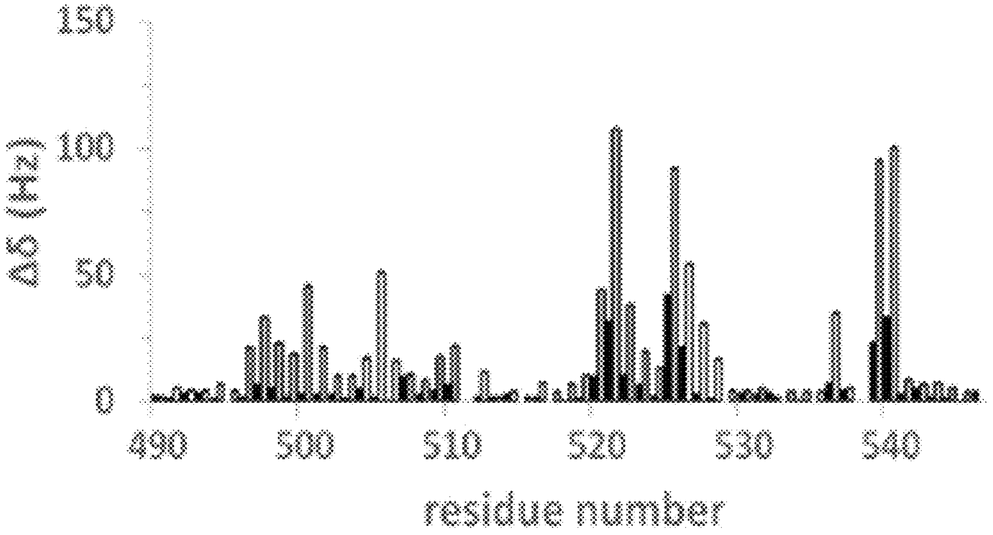

The two-surface interaction between SH3 and PRR2 was further confirmed in the NMR chemical shift perturbation (CSP) data, as the strongest effects were observed for both the canonical binding surface (Y497, Q500, D505, W525, A539, N540) as well as residues near the second surface (M520, I521, D522, W526) (FIG. 6B). Furthermore, the Y722A mutation (SEQ ID No: 5) reduced affinity 3.5-fold, and the A720-726 deletion mutant (SEQ ID No: 6) demonstrated a 27-fold loss of affinity and most significant CSP reductions at surface II residues I521 and L536 (FIGS. 6C-6D). Overall, the cortactin-Pyk2 interaction was found to span an extended proline-rich motif, including the canonical class II binding sequence and an additional C-terminal tripeptide extension with a second contributing binding surface.

Figure 7A:
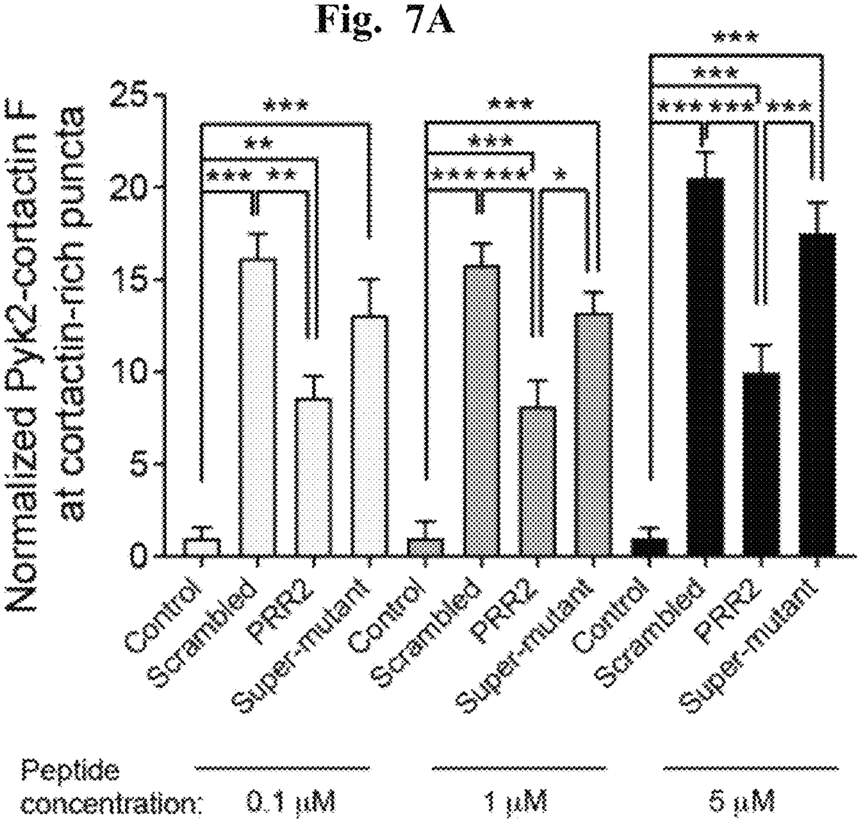
FIGS. 7A-7D show that a Pyk2-PRR2 super-mutant peptide does not inhibit the interaction between Pyk2 and cortactin at invadopodia.
Figure 7B:
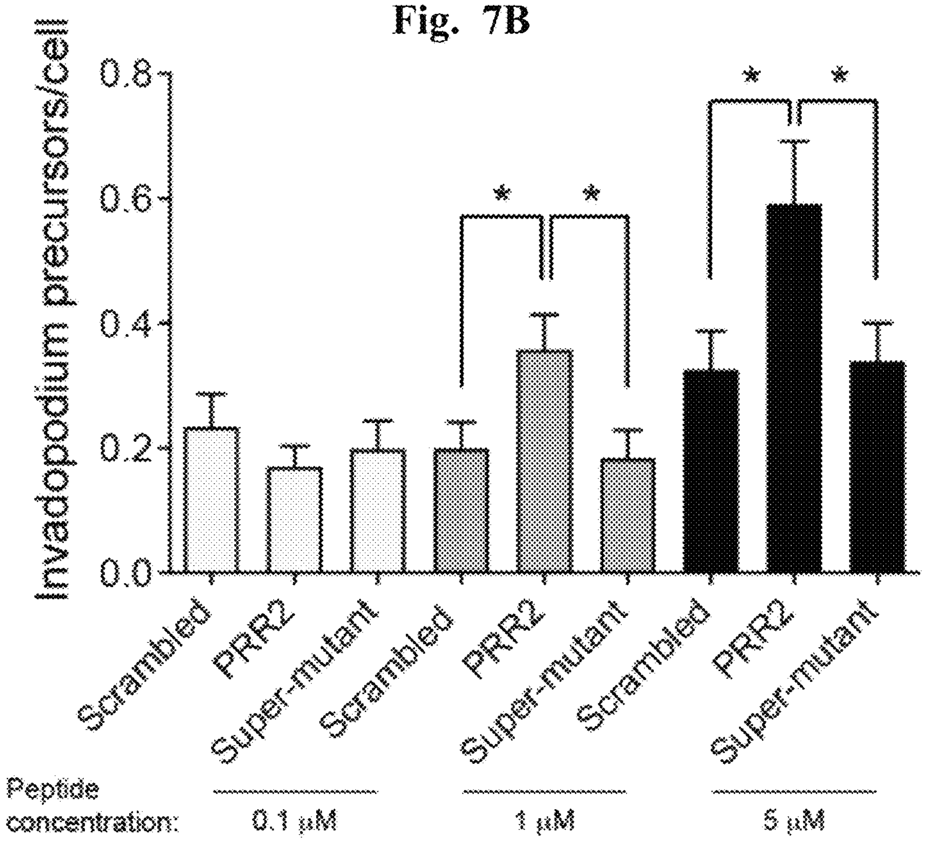
Figure 7C:
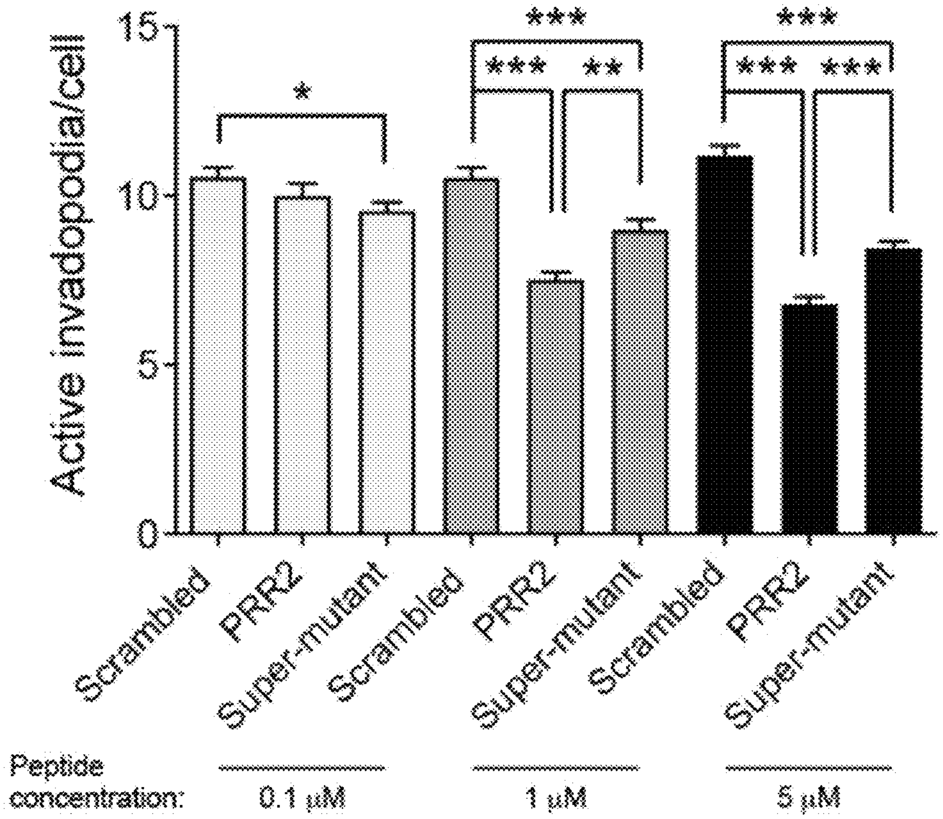
Figure 7D:
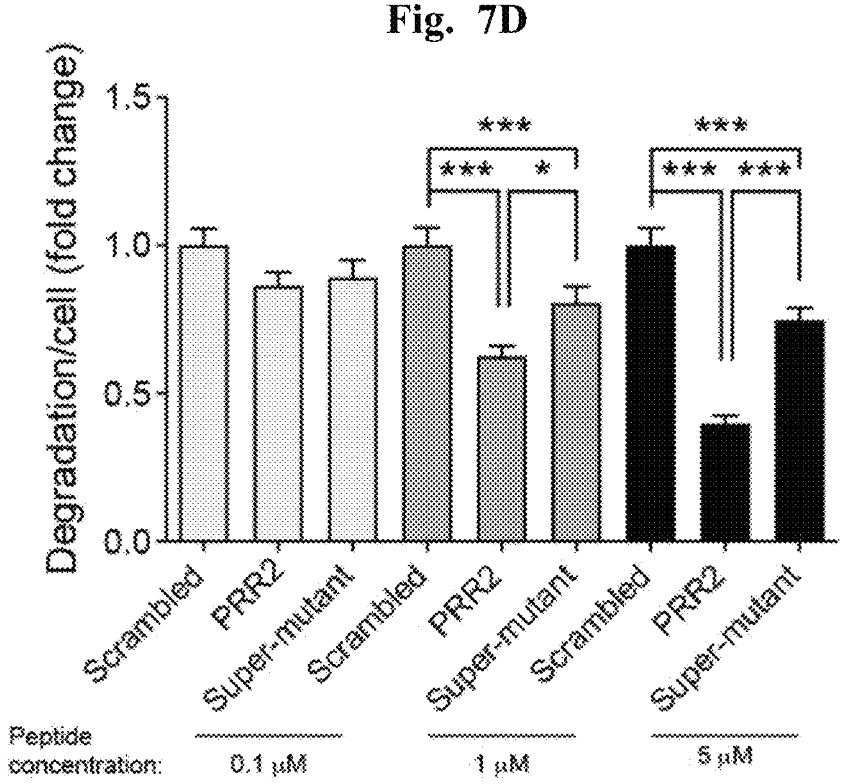

Example 7: A Super-Mutant Peptide Cannot Inhibit the Pyk2-Cortactin Interaction at Invadopodia and Spontaneous Lung Metastasis in a Xenograft Mouse Model A super-mutant Pyk2-PRR2 peptide (SEQ ID NO: 3) was synthesized, in which five critical amino acids were mutated (P714/717/720A, R719Q, K721Q). The loss of SH3 affinity of this peptide was verified by NMR, in which no detectable affinity could be observed (estimated $K_D$>1 mM). Similarly, FRET acceptor photobleaching experiments demonstrated that, unlike the Pyk2-PRR2 peptide, this super-mutant peptide does not significantly inhibit the Pyk2-cortactin interaction in invadopodia of breast tumor cells at any of the concentrations tested (FIG. 7A). The invadopodia assembly assay was repeated on fluorescently labeled gelatin matrix for control, Pyk2-PRR2, and super-mutant peptide, and labeled for Tks5 and cortactin. While no significant effect was observed for the super-mutant peptide in the number of invadopodium precursors formed in cells (FIG. 7B), a small but significant reduction was observed in the number of mature degrading invadopodia (FIG. 7C), and consequently, in the levels of ECM degradation (FIGS. 7D, compared to control peptide in both cases). Thus, although the super-mutant peptide cannot bind to the cortactin-SH3 domain in vitro or inhibit the cortactin-Pyk2 interaction in invadopodia, it can slightly (albeit less than Pyk2-PRR2) affect invadopodia maturation and subsequent ECM degradation. This residual effect may result from non-specific low-affinity binding of the remaining proline and tyrosine residues to the additional hydrophobic groove within the SH3 domain of cortactin.

Figure 8A:
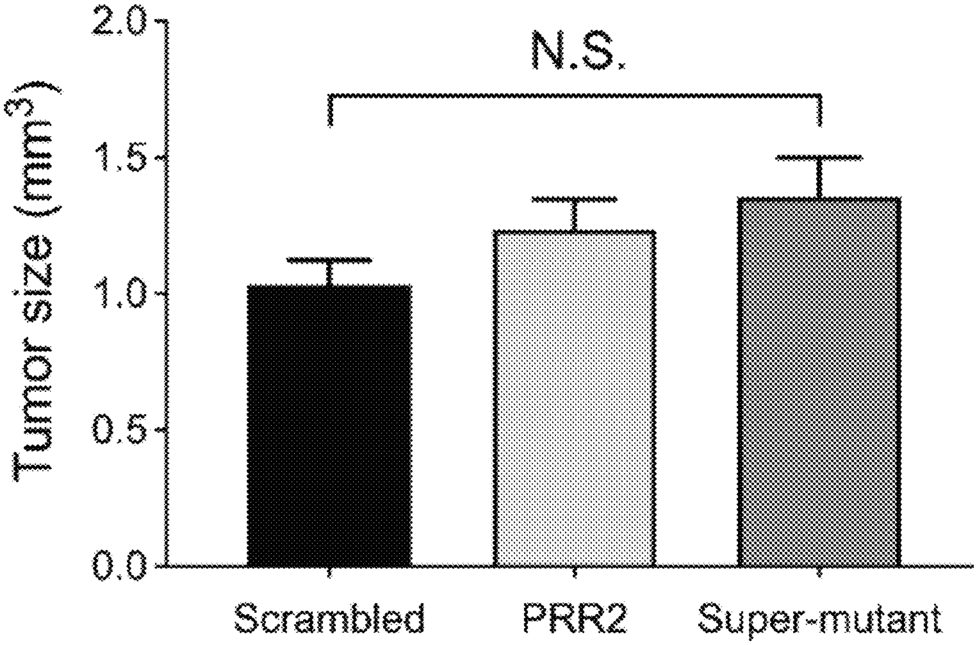
FIGS. 8A-8G show that the Pyk2 super-mutant peptide does not block spontaneous lung metastasis in a xenograft mouse model. 4T1 cells were injected into the mammary fat pad of 8-week-old BALB/c female mice and allowed to grow for 12 days until the tumors reached an average size of 100 $mm^3$. On day 13 following injection, mice were treated by intraperitoneal injection with 10 mg/kg of scrambled control, Pyk2-PRR2, or Pyk2 super-mutant once a day for eight days.
Figure 8B:
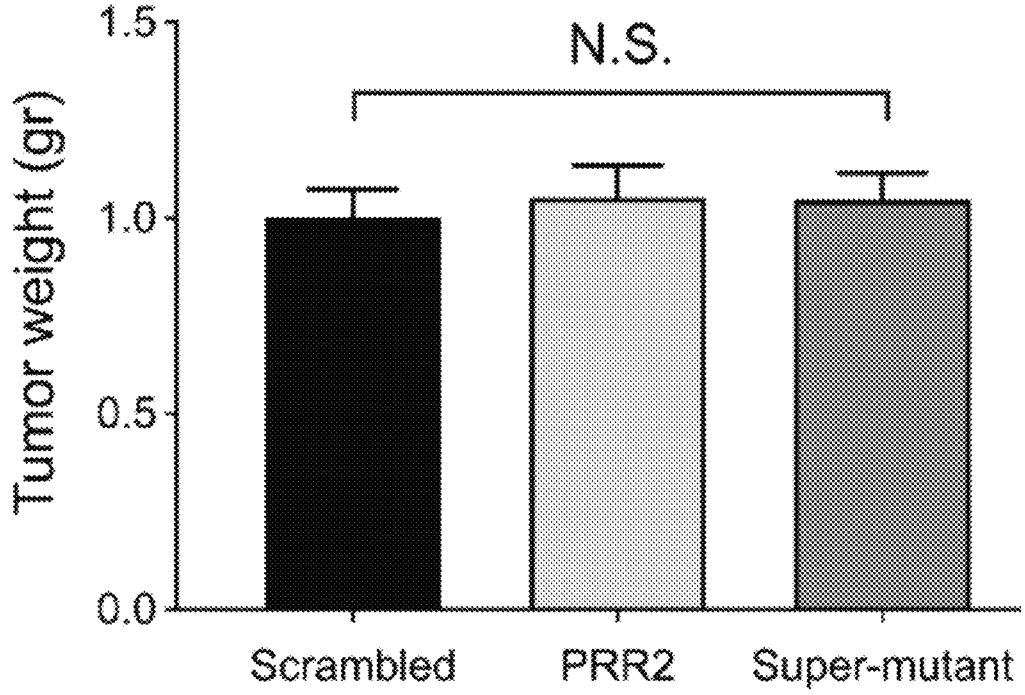
Figure 8C:
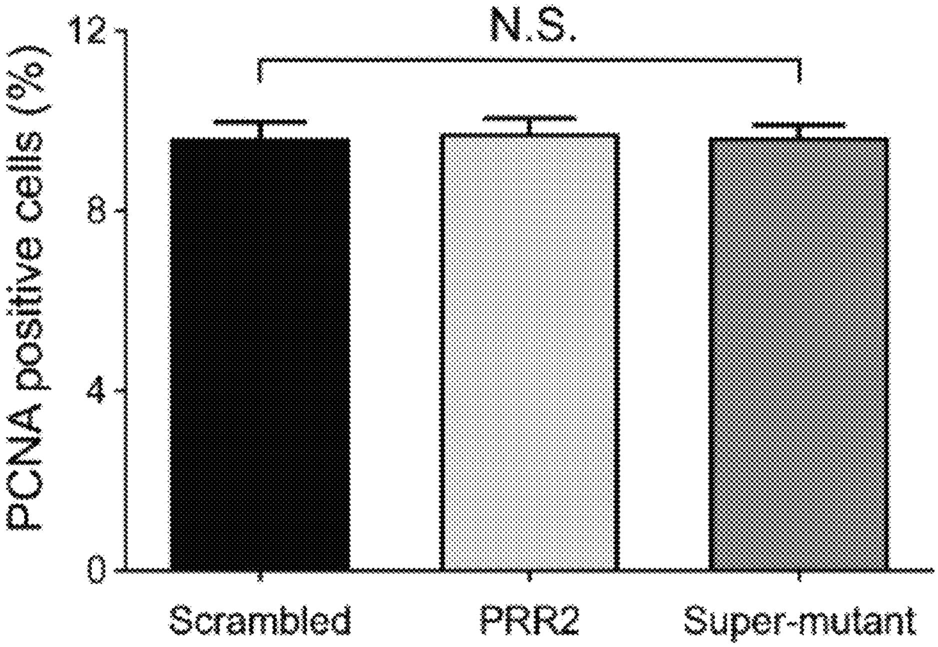
Figure 8D:
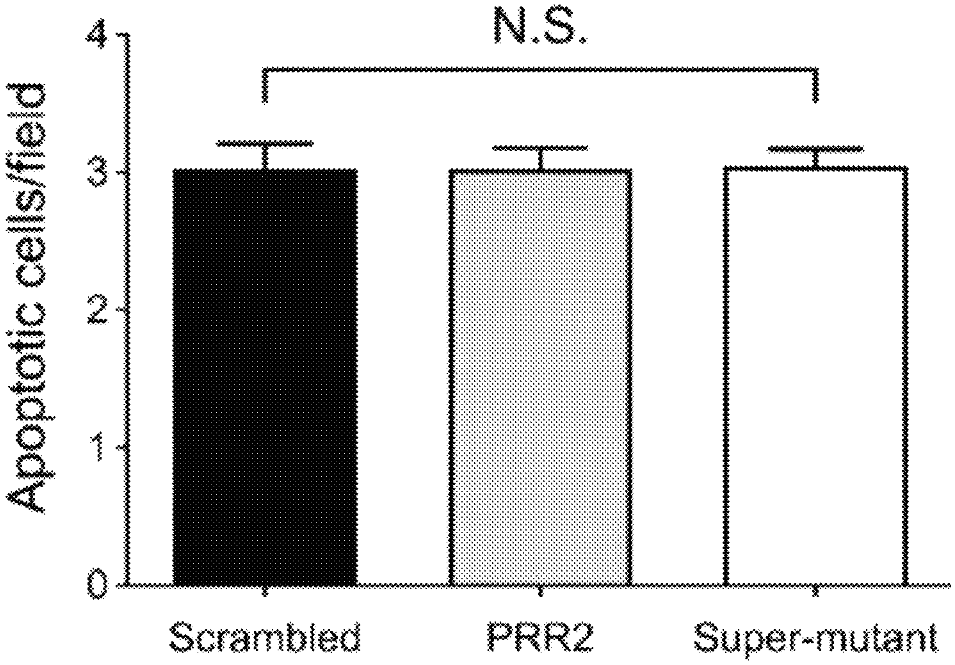
Figure 8E:
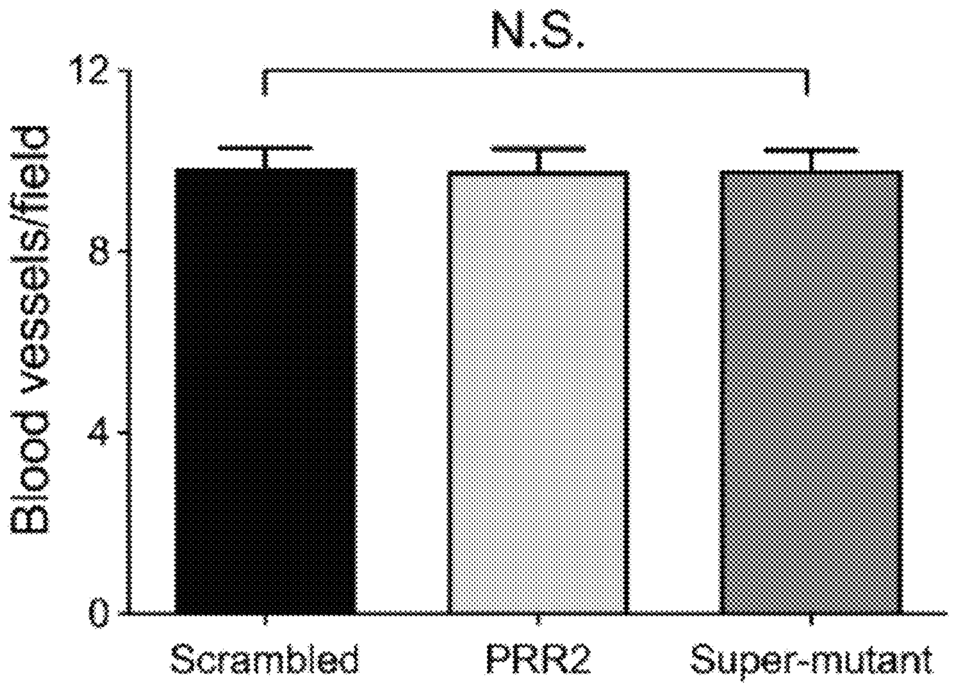
Figure 8F:
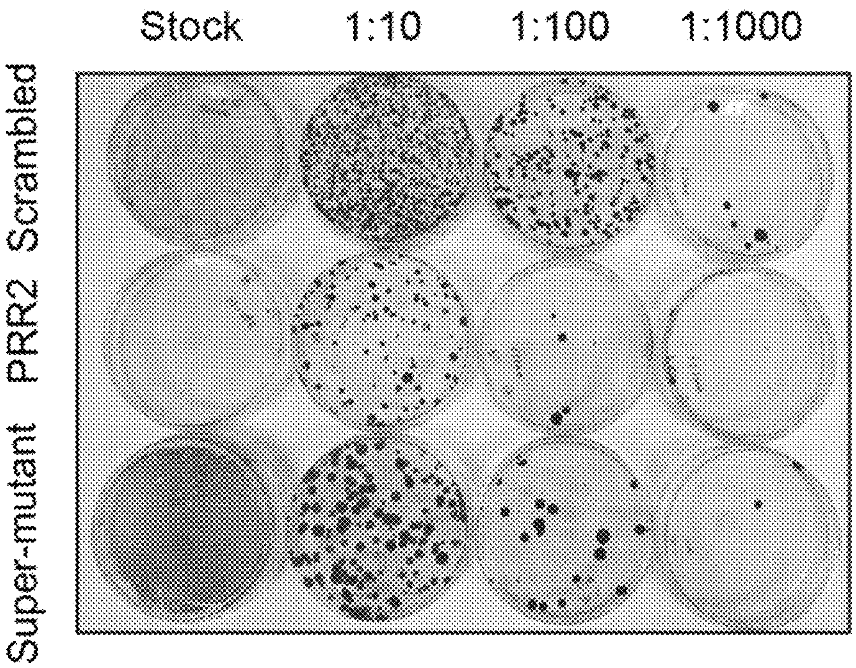
Figure 8G:
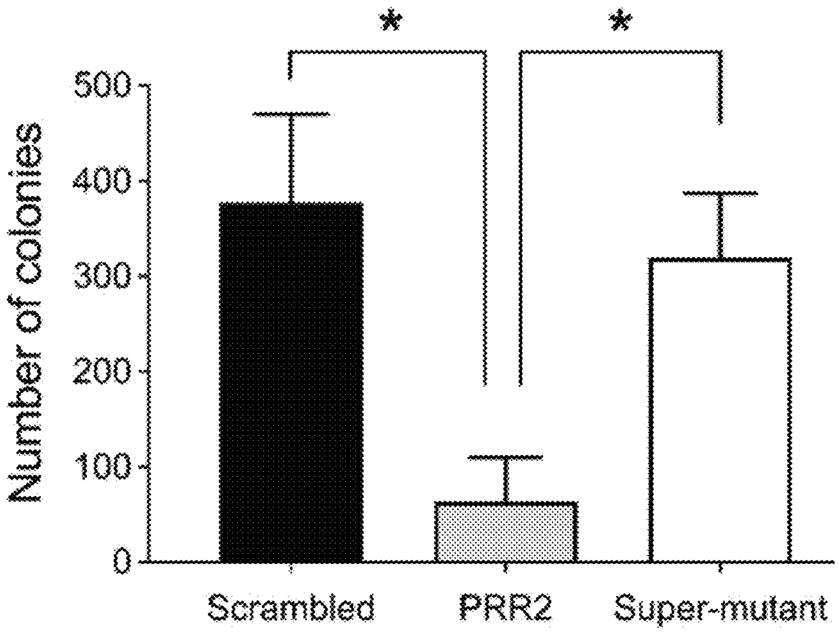

The xenograft model assay was also repeated with the Pyk2 super-mutant peptide, treating tumor-bearing mice with a cell-permeable Pyk2 super-mutant (with a scrambled peptide as control, SEQ ID NO: 4) by intraperitoneal injection for eight days. As above, no significant differences were detected in primary tumor growth in all groups (FIGS. 8A-8B), which was supported by similar proliferation, apoptosis, and angiogenesis traits of tumors in all peptide-treated mice (FIGS. 8C-8E). However, while Pyk2-PRR2 significantly inhibited lung metastasis, no significant differences in colony number, indicating lung metastasis, were observed between scrambled control and the Pyk2 super-mutant-treated tumor-bearing mice (FIGS. 8F-8G). These data demonstrate that, while the Pyk2 super-mutant peptide may have a residual effect on invadopodia maturation and function in vitro, it fails to inhibit spontaneous lung metastasis of breast tumor cells in vivo.

SEQUENCE LISTING

```
Sequence total quantity: 27
SEQ ID NO: 1            moltype = AA  length = 19
FEATURE                 Location/Qualifiers
source                  1..19
                        mol_type = protein
                        organism = synthetic construct
SEQUENCE: 1
TAFQEPPPKP SRPKYRPPP                                              19

SEQ ID NO: 2            moltype = AA  length = 16
FEATURE                 Location/Qualifiers
source                  1..16
                        mol_type = protein
                        organism = synthetic construct
SEQUENCE: 2
EFTGPPQKPP RLGAQS                                                 16

SEQ ID NO: 3            moltype = AA  length = 19
FEATURE                 Location/Qualifiers
source                  1..19
                        mol_type = protein
                        organism = synthetic construct
SEQUENCE: 3
TAFQEPAPKA SQAQYRPPP                                              19

SEQ ID NO: 4            moltype = AA  length = 19
FEATURE                 Location/Qualifiers
source                  1..19
                        mol_type = protein
                        organism = synthetic construct
SEQUENCE: 4
PEPYPTPAPF PKKQRPRPS                                              19

SEQ ID NO: 5            moltype = AA  length = 19
FEATURE                 Location/Qualifiers
source                  1..19
                        mol_type = protein
                        organism = synthetic construct
SEQUENCE: 5
TAFQEPPPKP SRPKARPPP                                              19

SEQ ID NO: 6            moltype = AA  length = 12
FEATURE                 Location/Qualifiers
source                  1..12
                        mol_type = protein
                        organism = synthetic construct
SEQUENCE: 6
TAFQEPPPKP SR                                                     12

SEQ ID NO: 7            moltype = AA  length = 26
FEATURE                 Location/Qualifiers
source                  1..26
                        mol_type = protein
                        organism = synthetic construct
SEQUENCE: 7
HAIYPRHTAF QEPPPKPSRP KYRPPP                                      26

SEQ ID NO: 8            moltype = AA  length = 26
FEATURE                 Location/Qualifiers
source                  1..26
                        mol_type = protein
                        organism = synthetic construct
SEQUENCE: 8
TAFQEPPPKP SRPKYRPPPH RPYIAH                                      26

SEQ ID NO: 9            moltype = AA  length = 19
FEATURE                 Location/Qualifiers
source                  1..19
                        mol_type = protein
                        organism = synthetic construct
SITE                    1
                        note = D-threonine
SITE                    2
                        note = D-alanine
SITE                    3
                        note = D-phenylalanine
SITE                    4
                        note = D-glutamine
```

```
SITE                   17..19
                       note = D-proline
SITE                   16
                       note = D-arginine
SEQUENCE: 9
TAFQEPPPKP SRPKYRPPP                                                19

SEQ ID NO: 10          moltype = AA  length = 7
FEATURE                Location/Qualifiers
source                 1..7
                       mol_type = protein
                       organism = synthetic construct
SEQUENCE: 10
HAIYPRH                                                             7

SEQ ID NO: 11          moltype = AA  length = 11
FEATURE                Location/Qualifiers
source                 1..11
                       mol_type = protein
                       organism = synthetic construct
SEQUENCE: 11
GRKKRRQRRR K                                                        11

SEQ ID NO: 12          moltype = AA  length = 9
FEATURE                Location/Qualifiers
source                 1..9
                       mol_type = protein
                       organism = synthetic construct
SEQUENCE: 12
PXXPXRPKY                                                           9

SEQ ID NO: 13          moltype = AA  length = 9
FEATURE                Location/Qualifiers
source                 1..9
                       mol_type = protein
                       organism = synthetic construct
SEQUENCE: 13
PXXPXRPRY                                                           9

SEQ ID NO: 14          moltype = AA  length = 9
FEATURE                Location/Qualifiers
source                 1..9
                       mol_type = protein
                       organism = synthetic construct
SEQUENCE: 14
PXXPXKPRY                                                           9

SEQ ID NO: 15          moltype = AA  length = 9
FEATURE                Location/Qualifiers
source                 1..9
                       mol_type = protein
                       organism = synthetic construct
SEQUENCE: 15
PXXPXKPKY                                                           9

SEQ ID NO: 16          moltype = AA  length = 9
FEATURE                Location/Qualifiers
source                 1..9
                       mol_type = protein
                       organism = synthetic construct
SEQUENCE: 16
PXXPXRPKW                                                           9

SEQ ID NO: 17          moltype = AA  length = 9
FEATURE                Location/Qualifiers
source                 1..9
                       mol_type = protein
                       organism = synthetic construct
SEQUENCE: 17
PXXPXRPRW                                                           9

SEQ ID NO: 18          moltype = AA  length = 9
FEATURE                Location/Qualifiers
source                 1..9
                       mol_type = protein
                       organism = synthetic construct
SEQUENCE: 18
PXXPXKPRW                                                           9
```

-continued

```
SEQ ID NO: 19          moltype = AA  length = 9
FEATURE                Location/Qualifiers
source                 1..9
                       mol_type = protein
                       organism = synthetic construct
SEQUENCE: 19
PXXPXKPKW                                                    9

SEQ ID NO: 20          moltype = AA  length = 9
FEATURE                Location/Qualifiers
source                 1..9
                       mol_type = protein
                       organism = synthetic construct
SEQUENCE: 20
PXXPXRPKF                                                    9

SEQ ID NO: 21          moltype = AA  length = 9
FEATURE                Location/Qualifiers
source                 1..9
                       mol_type = protein
                       organism = synthetic construct
SEQUENCE: 21
PXXPXRPRF                                                    9

SEQ ID NO: 22          moltype = AA  length = 9
FEATURE                Location/Qualifiers
source                 1..9
                       mol_type = protein
                       organism = synthetic construct
SEQUENCE: 22
PXXPXKPRF                                                    9

SEQ ID NO: 23          moltype = AA  length = 9
FEATURE                Location/Qualifiers
source                 1..9
                       mol_type = protein
                       organism = synthetic construct
SEQUENCE: 23
PXXPXKPKF                                                    9

SEQ ID NO: 24          moltype = AA  length = 9
FEATURE                Location/Qualifiers
source                 1..9
                       mol_type = protein
                       organism = synthetic construct
SEQUENCE: 24
PPKPSRPKY                                                    9

SEQ ID NO: 25          moltype = AA  length = 7
FEATURE                Location/Qualifiers
source                 1..7
                       mol_type = protein
                       organism = synthetic construct
VARIANT                3
                       note = A, V, L, I, G, M
SEQUENCE: 25
PPXPXKP                                                      7

SEQ ID NO: 26          moltype = AA  length = 8
FEATURE                Location/Qualifiers
source                 1..8
                       mol_type = protein
                       organism = synthetic construct
SEQUENCE: 26
PPPKPSRP                                                     8

SEQ ID NO: 27          moltype = AA  length = 8
FEATURE                Location/Qualifiers
source                 1..8
                       mol_type = protein
                       organism = synthetic construct
SEQUENCE: 27
PPQKPPRL                                                     8
```

The invention claimed is:

1. An isolated Proline-rich tyrosine kinase 2 (Pyk2)-derived peptide comprising a consensus proline-rich region 2 (PRR2) sequence corresponding to positions 7-15 of SEQ ID NO: 1 and defined as PxxPx(R/K)P(K/R)(Y/W/F), wherein: the second position of the consensus, corresponding to position 8 of SEQ ID NO: 1, is proline; "x" at positions 3 and 5 of the consensus, corresponding to positions 9 and 11 of SEQ ID NO: 1, respectively, represents any amino acid; the peptide has a length of 10-30 amino acids; and the peptide is capable of inhibiting metastasis by binding to a Src homology 3 (SH3) domain of cortactin.

2. The isolated Pyk2-derived peptide of claim 1, wherein the peptide comprises a sequence at least 80% identical to PPPKPSRP (SEQ ID NO: 26), or PPKPSRPKY (SEQ ID NO: 24), or comprises the consensus sequence PxxPxRPKY (SEQ ID NO: 12).

3. The isolated Pyk2-derived peptide of claim 1, comprising a sequence at least 80%, identical to the sequence set forth in SEQ ID NO: 1.

4. The isolated Pyk2-derived peptide of claim 1, comprising at least one proline outside the consensus PRR2 sequence.

5. The isolated Pyk2-derived peptide of claim 1, further comprising a least one tag sequence selected from the group consisting of HIV-TAT, HAIYPRH, and combinations thereof.

6. The isolated Pyk2-derived peptide of claim 1, comprising at least one non-conventional amino acid and/or at least one modified amino acid.

7. The isolated Pyk2-derived peptide of claim 6, wherein the at least one non-conventional amino acid and/or modified amino acid is outside the consensus PRR2 sequence.

8. The isolated Pyk2-derived peptide of claim 1, wherein the peptide is a cyclic peptide.

9. The isolated Pyk2-derived peptide of claim 1, wherein the peptide does not inhibit primary tumor growth.

10. A method of treating a cancer in a subject, the method comprising administering to the subject a therapeutically-effective dose of the isolated Proline-rich tyrosine kinase 2 (Pyk2)-derived peptide of claim 1.

11. The method of claim 10, wherein the treating comprises inhibiting or preventing cancer invasion and/or cancer metastasis in the subject.

12. The method of claim 10, further comprising administering to the subject an anti-cancer treatment.

13. The method of claim 10, wherein the cancer comprises invadopodia.

14. The method of claim 10, wherein the cancer is invasive or metastatic.

15. The method of claim 10, wherein the cancer is not invasive or does not comprise metastases.

16. The method of claim 10, wherein the cancer is selected from the group consisting of breast cancer, pancreatic cancer, head and neck cancer, prostate cancer, fibrosarcoma, and melanoma.

17. The method of claim 10, wherein the administration is intravenous, intramuscular, subcutaneous, intratumoral, or intraperitoneal.

18. The isolated Pyk2-derived peptide of claim 1, wherein the amino acid at the eighth position of the consensus PRR2 sequence PxxPx(R/K)P(K/R)(Y/W/F), corresponding to position 14 of SEQ ID NO: 1, is a lysine.

* * * * *